United States Patent
Asano

(10) Patent No.: US 9,188,858 B2
(45) Date of Patent: Nov. 17, 2015

(54) RADIATION-SENSITIVE RESIN COMPOSITION, METHOD FOR FORMING RESIST PATTERN, ACID GENERATING AGENT AND COMPOUND

(71) Applicant: JSR CORPORATION, Tokyo (JP)

(72) Inventor: Yusuke Asano, Tokyo (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 13/627,208

(22) Filed: Sep. 26, 2012

(65) Prior Publication Data

US 2013/0078579 A1    Mar. 28, 2013

(30) Foreign Application Priority Data

Sep. 26, 2011 (JP) ................................. 2011-210002
Sep. 6, 2012 (JP) ................................. 2012-196209

(51) Int. Cl.

| | |
|---|---|
| *G03F 7/004* | (2006.01) |
| *C07C 309/19* | (2006.01) |
| *C07C 309/12* | (2006.01) |
| *C07C 381/12* | (2006.01) |
| *G03F 7/20* | (2006.01) |
| *G03F 7/039* | (2006.01) |
| *G03F 7/11* | (2006.01) |
| *C07C 309/07* | (2006.01) |
| *C07C 309/16* | (2006.01) |
| *C07C 309/17* | (2006.01) |
| *C07C 309/65* | (2006.01) |
| *C07C 317/12* | (2006.01) |
| *C07D 295/185* | (2006.01) |

(52) U.S. Cl.

CPC ............ *G03F 7/0045* (2013.01); *C07C 309/07* (2013.01); *C07C 309/12* (2013.01); *C07C 309/16* (2013.01); *C07C 309/17* (2013.01); *C07C 309/19* (2013.01); *C07C 309/65* (2013.01); *C07C 317/12* (2013.01); *C07C 381/12* (2013.01); *C07D 295/185* (2013.01); *G03F 7/0046* (2013.01); *G03F 7/0397* (2013.01); *G03F 7/11* (2013.01); *G03F 7/20* (2013.01); *G03F 7/2041* (2013.01); *C07C 2101/14* (2013.01); *C07C 2102/42* (2013.01); *C07C 2103/74* (2013.01)

(58) Field of Classification Search
None
See application file for complete search history.

(56) References Cited

U.S. PATENT DOCUMENTS

| | | | |
|---|---|---|---|
| 2002/0102491 A1* | 8/2002 | Kodama et al. | ............ 430/270.1 |
| 2010/0015555 A1* | 1/2010 | Utsumi et al. | ............ 430/286.1 |
| 2010/0121077 A1* | 5/2010 | Seshimo et al. | ................ 549/31 |
| 2010/0196820 A1* | 8/2010 | Kawaue et al. | ............ 430/270.1 |

FOREIGN PATENT DOCUMENTS

| | | |
|---|---|---|
| JP | 06-12452 B2 | 5/1984 |
| JP | 59-93448 | 5/1984 |
| JP | 05-188598 | 7/1993 |
| JP | 2002-214774 A | 7/2002 |
| JP | 2005-352384 | 12/2005 |
| JP | 2006-162735 A | 6/2006 |
| JP | 2008-299069 A | 12/2008 |
| JP | 2008297255 A * | 12/2008 |
| JP | 2010-204646 | 9/2010 |
| JP | 2010-215608 | 9/2010 |
| WO | WO 2007/116664 | 10/2007 |

OTHER PUBLICATIONS

Machine translation JP 2008-297255. Dec. 11, 2008.*
Office Action issued Sep. 29, 2015, in Japanese Patent Application No. 2012-196209 filed Sep. 6, 2012 (w/ English translation).

* cited by examiner

*Primary Examiner* — Cynthia H Kelly
*Assistant Examiner* — Alyssa L Cepluch
(74) *Attorney, Agent, or Firm* — Oblon, McClelland, Maier & Neustadt, L.L.P.

(57) ABSTRACT

A radiation-sensitive resin composition includes an acid generating agent to generate a compound represented by a following formula (1) by irradiation with a radioactive ray. In the formula (1), $R^1$ represents a monovalent organic group having 1 to 20 carbon atoms. $R^2$ represents a hydrogen atom or a monovalent organic group having 1 to 20 carbon atoms. The compound represented by the formula (1) is preferably a compound represented by a following formula (1-1). In the formula (1-1), $R^2$ is as defined in the above formula (1). X represents an electron attractive group. $R^3$ represents a monovalent organic group having 1 to 20 carbon atoms.

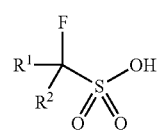

(1)

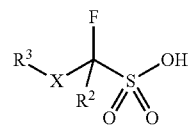

(1-1)

18 Claims, No Drawings

RADIATION-SENSITIVE RESIN COMPOSITION, METHOD FOR FORMING RESIST PATTERN, ACID GENERATING AGENT AND COMPOUND

CROSS-REFERENCE TO RELATED APPLICATIONS

The present application claims priority under 35 U.S.C. §119 to Japanese Patent Application No. 2011-210002, filed Sep. 26, 2011, and to Japanese Patent Application No. 2012-196209, filed Sep. 6, 2012. The contents of these applications are incorporated herein by reference in their entirety.

BACKGROUND OF THE INVENTION

1. Field of the Invention

The present invention relates to a radiation-sensitive resin composition, a method for forming a resist pattern, an acid generating agent and a compound.

2. Discussion of the Background

In the field of microfabrication represented by manufacturing of integrated circuit elements, in order to obtain higher integrity, microfabrication at a level of no greater than 100 nm has been recently required. As radioactive rays used for such microfabrication, for example, a KrF excimer laser beam (wavelength: 248 nm), an ArF excimer laser beam (wavelength: 193 nm), an F2 excimer laser beam (wavelength: 157 nm), EUV light (wavelength: 13 nm), an electron beam and the like have attracted attention.

With attention to such radioactive rays, a number of photoresist materials have been proposed. The photoresist materials are exemplified by a composition which contains a polymer component having an acid-dissociable group and an acid generating agent component that generates an acid by irradiation with a radioactive ray (exposure), and utilizes a chemical amplification effect between these components, and the like. As the acid generating agent, difluorosulfonic acid type sulfonium salts were developed hitherto (see Japanese Unexamined Patent Application, Publication Nos. 2010-215608 and 2010-204646).

Not only improvement of basic characteristics such as sensitivity and resolving ability but also improvement of LWR (Line Width Roughness), exposure latitude and the like has been desired for a radiation-sensitive resin composition for forming a finer resist pattern.

SUMMARY OF THE INVENTION

According to one aspect of the present invention, a radiation-sensitive resin composition includes an acid generating agent to generate a compound represented by a following formula (1) by irradiation with a radioactive ray.

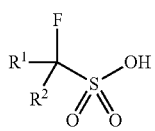
(1)

In the formula (1), $R^1$ represents a monovalent organic group having 1 to 20 carbon atoms. $R^2$ represents a hydrogen atom or a monovalent organic group having 1 to 20 carbon atoms.

According to another aspect of the present invention, a method for forming a resist pattern includes providing the radiation-sensitive resin composition on a substrate to form a resist film. The resist film formed is exposed. The resist film exposed is developed.

According to further aspect of the present invention, an acid generating agent generates a compound represented by a following formula (1) by irradiation with a radioactive ray.

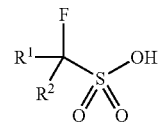
(1)

In the formula (1), $R^1$ represents a monovalent organic group having 1 to 20 carbon atoms. $R^2$ represents a hydrogen atom or a monovalent organic group having 1 to 20 carbon atoms.

According to further aspect of the present invention, a compound is represented by a following formula (1).

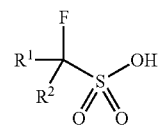
(1)

In the formula (1), $R^1$ represents a monovalent organic group having 1 to 20 carbon atoms. $R^2$ represents a hydrogen atom or a monovalent organic group having 1 to 20 carbon atoms.

DESCRIPTION OF THE EMBODIMENTS

An aspect of the embodiments of the present invention made for solving the foregoing problems provides a radiation-sensitive resin composition including (A1) an acid generating agent that generates a compound represented by the following formula (1) upon irradiation with a radioactive ray (hereinafter, may be also referred to as "specified acid generating agent (A1)"):

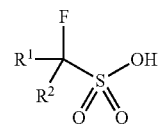
(1)

wherein, in the formula (1), $R^1$ represents a monovalent organic group having 1 to 20 carbon atoms; and $R^2$ represents a hydrogen atom or a monovalent organic group having 1 to 20 carbon atoms.

The specified acid generating agent (A1) contained in the radiation-sensitive resin composition is a monofluorosulfonic acid type acid generating agent that generates the compound represented by the above formula (1). Thus, an acid having lower acidity is generated upon exposure as compared with conventional difluorosulfonic acid type acid generating agents; therefore, LWR of the resist pattern formed from the radiation-sensitive resin composition can be improved.

The compound represented by the above formula (1) is preferably a compound represented by the following formula (1-1):

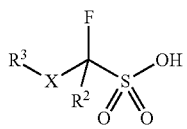

(1-1)

wherein, in the formula (1-1), $R^2$ is as defined in the above formula (1); X represents an electron attractive group; and $R^3$ represents a monovalent organic group having 1 to 20 carbon atoms.

When the compound represented by the above formula (1) is a compound represented by the above formula (1-1) in which an electron attractive group is bound to a carbon atom to which a sulfo group bonds, acidity of an acid generated from the specified acid generating agent (A1) can be appropriately adjusted, and as a result, the LWR of the resist pattern formed from the radiation-sensitive resin composition can be more improved.

X in the above formula (1-1) preferably represents a carbonyl group. When a carbonyl group is introduced as the electron attractive group X, the acidity of an acid generated from the specified acid generating agent (A1) can be more appropriately adjusted, and consequently the LWR of the resist pattern formed from the radiation-sensitive resin composition can be more improved.

$R^3$ in the above formula (1-1) preferably represents a monovalent alicyclic hydrocarbon group having 3 to 20 carbon atoms and not having or optionally having a substituent, or a monovalent aromatic hydrocarbon group having 6 to 20 carbon atoms and not having or optionally having a substituent. When $R^3$ represents a group having the specific structure having appropriate bulkiness, diffusion of an acid generated from the specified acid generating agent (A1) can be appropriately suppressed, and consequently the LWR of the resist pattern formed from the radiation-sensitive resin composition can be more improved.

$R^2$ in the above formula (1-1) preferably represents a hydrogen atom. When $R^2$ represents a hydrogen atom, the acidity of the acid generated from the specified acid generating agent (A1) can be further appropriately adjusted, and consequently the LWR of the resist pattern formed from the radiation-sensitive resin composition can be more improved.

The acid generating agent (A1) is preferably a sulfonium salt compound or an iodonium salt compound. When the specified acid generating agent (A1) is provided in the form of the specified salt compound, radiation sensitivity of the specified acid generating agent (A1) can be more improved.

Another aspect of the embodiments of the present invention provides a method for forming a resist pattern, the method including:

(1) forming a resist film on a substrate using the radiation-sensitive resin composition;

(2) exposing the resist film formed; and (3) developing the resist film exposed.

According to the formation method, a resist pattern having satisfactory LWR can be formed since the radiation-sensitive resin composition is used.

The exposure in the step (2) is preferably carried out by liquid immersion lithography. Since the formation method can adopt even a liquid immersion lithography step, a finer resist pattern can be formed, and is thus suitable for a lithography process by which microfabrication is expected to further advance in the future.

Still another aspect of the embodiments of the present invention involves an acid generating agent that generates by irradiation with a radioactive ray, a compound represented by the following formula (1):

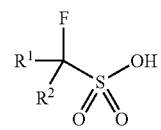

(1)

wherein, in the formula (1), $R^1$ represents a monovalent organic group having 1 to 20 carbon atoms; and $R^2$ represents a hydrogen atom or a monovalent organic group having 1 to 20 carbon atoms.

Since the acid generating agent is a monofluorosulfonic acid type acid generating agent, an acid having lower acidity is generated upon exposure as compared with conventional difluorosulfonic acid type acid generating agents; therefore, radiation-sensitive resin composition containing the acid generating agent can form a resist pattern having satisfactory LWR.

The compound represented by the above formula (1) is preferably a compound represented by the following formula (1-1). In addition, X in the above formula (1-1) is preferably a carbonyl group.

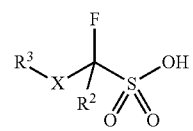

(1-1)

In the formula (1-1), $R^2$ is as defined in the above formula (1); X represents an electron attractive group; and $R^3$ represents a monovalent organic group having 1 to 20 carbon atoms.

Yet another aspect of the embodiments of the present invention involves a compound represented by the following formula (1):

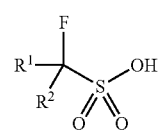

(1)

wherein, in the formula (1), $R^2$ represents a monovalent organic group having 1 to 20 carbon atoms; and $R^2$ represents a hydrogen atom or a monovalent organic group having 1 to 20 carbon atoms.)

The compound is suitable as a basic material for producing the acid generating agent of the embodiment of the present invention, and the like.

The compound represented by the above formula (1) is preferably a compound represented by the following formula (1-1). Additionally, X in the above formula (1-1) is preferably a carbonyl group.

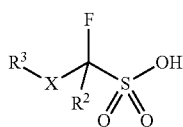
(1-1)

In the formula (1-1), $R^2$ is as defined in the above formula (1); X represents an electron attractive group; and $R^3$ represents a monovalent organic group having 1 to 20 carbon atoms.

The compound represented by the above formula (1) can be more readily synthesized by binding of the electron attractive group X to the carbon atom to which the sulfo group bonds, and can be further readily synthesized when the electron attractive group X is a carbonyl group.

According to the embodiment of the present invention, a radiation-sensitive resin composition capable of forming a resist pattern having satisfactory LWR can be provided. Also, the method for forming a resist pattern in which the radiation-sensitive resin composition is used can adopt even a liquid immersion lithography step, whereby formation of a finer resist pattern is enabled. The radiation-sensitive resin composition containing the acid generating agent of the embodiment of the present invention can form a resist pattern having satisfactory LWR. The compound of the embodiment of the present invention is suitable as a basic material for producing the acid generating agent, and the like. Therefore, these can be suitably used for a lithography process by which microfabrication is expected to further advance in the future. The embodiments will now be described in detail.

<Radiation-Sensitive Resin Composition>

The radiation-sensitive resin composition of the embodiment of the present invention contains the specified acid generating agent (A1). In addition, the radiation-sensitive resin composition may contain as a suitable component (B) a base polymer, (C) a fluorine atom-containing polymer and (D) an acid diffusion control agent. Furthermore, the radiation-sensitive resin composition may contain other optional component. Hereinafter, each component is described in detail.

<(A1) Specified Acid Generating Agent>

The specified acid generating agent (A1) is an acid generating agent that generates the compound represented by the above formula (1) by irradiation with a radioactive ray.

In the above formula (1), $R^2$ represents a monovalent organic group having 1 to 20 carbon atoms; and $R^2$ represents a hydrogen atom or a monovalent organic group having 1 to 20 carbon atoms.

The monovalent organic group having 1 to 20 carbon atoms represented by the $R^2$ and $R^2$ is exemplified by a hydrocarbon group having 1 to 20 carbon atoms; an organic group having 1 to 20 carbon atoms in total and having at least one selected from the group consisting of an ether bond, a carbonyl group, an ester group and a sulfonyl group, and the like.

The hydrocarbon group having 1 to 20 carbon atoms is exemplified by a monovalent alkyl group having 1 to 20 carbon atoms, an alicyclic hydrocarbon group having 3 to 20 carbon atoms, an aromatic hydrocarbon group having 6 to 20 carbon atoms, and the like. These groups are unsubstituted or optionally substituted with, for example, a halogen atom, a hydroxyl group, a thiol group, an aryl group, an alkenyl group, or the like.

Examples of the alkyl group having 1 to 20 carbon atoms include a methyl group, an ethyl group, a linear or branched propyl group, a butyl group, a pentyl group, a hexyl group, a heptyl group, an octyl group, a nonyl group, a decyl group, a dodecyl group, a tridecyl group, a tetradecyl group, a pentadecyl group, a hexadecyl group, a heptadecyl group, an octadecyl group, a nonadecyl group, an eicosyl group, and the like. Examples of the alicyclic hydrocarbon group having 3 to 20 carbon atoms include a cyclopropyl group, a cyclobutyl group, a cyclopentyl group, a cyclohexyl group, a norbornyl group, an adamantyl group, and the like. Examples of the aromatic hydrocarbon group having 6 to 20 carbon atoms include a phenyl group, a benzyl group, and the like.

Examples of the organic group having 1 to 20 carbon atoms in total and having an ether bond include alkoxy groups having 1 to 20 carbon atoms, alkenyloxy groups having 2 to 20 carbon atoms, alkynyloxy groups having 2 to 20 carbon atoms, aryloxy groups having 6 to 12 carbon atoms, alkoxyalkyl groups having 2 to 20 carbon atoms, and the like. Specific examples are a methoxy group, an ethoxy group, a propoxy group, an isopropyloxy group, a butoxy group, a phenoxy group, a propenyloxy group, a cyclohexyloxy group, a methoxymethyl group, and the like. Examples of the organic group having 1 to 20 carbon atoms in total and having a carbonyl group include acyl groups having 2 to 20 carbon atoms, and the like. Specific examples are an acetyl group, a propionyl group, an isopropionyl group, a benzoyl group, and the like. Examples of the organic group having 1 to 20 carbon atoms in total and having an ester group include acyloxy groups having 2 to 20 carbon atoms, and the like. Specific examples are an acetyloxy group, a propionyloxy group, an isopropionyloxy group and a benzoyloxy group, and the like. Examples of the organic group having 1 to 20 carbon atoms in total and having a sulfonyl group include alkylsulfonyl groups having 1 to 20 carbon atoms, cycloalkylsulfonyl groups having 3 to 20 carbon atoms, arylsulfonyl groups having 6 to 20 carbon atoms, and the like. Specific examples include a methanesulfonyl group, a toluenesulfonyl group, and the like.

The compound represented by the above formula (1) is preferably the compound represented by the above formula (1-1). In the above formula (1-1), $R^2$ is as defined in the above formula (1); X represents an electron attractive group; and $R^3$ represents a monovalent organic group having 1 to 20 carbon atoms. When the compound represented by the above formula (1) is the compound represented by the above formula (1-1) in which an electron attractive group is bound to a carbon atom to which a sulfo group bonds, acidity of an acid generated from the specified acid generating agent (A1) can be appropriately adjusted, and as a result, the LWR of the resist pattern formed from the radiation-sensitive resin composition can be more improved.

Examples of the electron attractive group represented by the X include —CO—, —CONH—, —COO—, —C(=NR')—, —SO—, —SO$_2$—, a group represented by the following formula (a), and the like. R' represents a hydrogen atom or a monovalent hydrocarbon group having 1 to 20 carbon atoms.

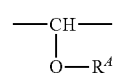
(a)

In the above formula (a), $R^4$ represents a hydrogen atom, a monovalent hydrocarbon group having 1 to 20 carbon atoms or an acyl group having 1 to 20 carbon atoms.

Examples of the monovalent hydrocarbon group represented by the R' and $R^4$ include alkyl groups such as a methyl group, an ethyl group, a n-propyl group, an i-propyl group, a n-butyl group, a n-hexyl group, a n-octyl group, a n-nonyl group and a n-decyl group;

alkenyl groups such as an ethenyl group, a propenyl group and a butenyl group;

alkynyl groups such as an ethynyl group, a propynyl group and a butynyl group;

cycloalkyl groups such as a cyclopropyl group, a cyclopentyl group, a cyclohexyl group, a cyclooctyl group, a norbornyl group and an adamantyl group;

cycloalkenyl groups such as a cyclopentenyl group, a cyclohexenyl group and a norbornenyl group;

aryl groups such as a phenyl group, a tolyl group, a xylyl group and a naphthyl group;

aralkyl groups such as a benzyl group, a phenethyl group and a naphthylmethyl group, and the like.

Examples of the acyl group represented by the $R^4$ include groups derived from a saturated aliphatic carboxylic acid such as a formyl group, an acetyl group, a propionyl group, a butyryl group, a pentanoyl group, a hexanoyl group, a heptanoyl group, an octanoyl group, a nonanoyl group, a decanoyl group, an undecanoyl group and a dodecanoyl group;

groups derived from an alicyclic carboxylic acid such as a norbornanecarbonyl group and an adamantanecarbonyl group;

groups derived from an unsaturated aliphatic carboxylic acid such as an acryloyl group, a methacryloyl group and a propioloyl group;

groups derived from an aromatic carboxylic acid such as a benzoyl group, a toluoyl group and a naphthoyl group, and the like.

X preferably represents a carbonyl group (—CO—). When a carbonyl group is introduced as the electron attractive group X, the acidity of the acid generated from the specified acid generating agent (A1) can be more appropriately adjusted, and consequently the LWR of the resist pattern formed from the radiation-sensitive resin composition can be more improved.

$R^2$ preferably represents a hydrogen atom. When the $R^2$ represents a hydrogen atom, the acidity of the acid generated from the specified acid generating agent (A1) can be further appropriately adjusted, and consequently the LWR of the resist pattern formed from the radiation-sensitive resin composition can be more improved.

The monovalent organic group having 1 to 20 carbon atoms represented by the $R^3$ is exemplified by groups exemplified as the monovalent organic group having 1 to 20 carbon atoms represented by the $R^1$ and $R^2$. $R^3$ is exemplified by a monovalent alicyclic hydrocarbon group having 3 to 20 carbon atoms and not having or optionally having a substituent, or a monovalent aromatic hydrocarbon group having 6 to 20 carbon atoms and not having or optionally having a substituent. Examples of the substituent include a hydroxyl group, a thiol group, an aryl group, an alkenyl group, and the like. When the $R^3$ represents a monovalent alicyclic hydrocarbon group having 3 to 20 carbon atoms and not having or optionally having a substituent, or a monovalent aromatic hydrocarbon group having 6 to 20 carbon atoms and not having or optionally having a substituent each having appropriate bulkiness, diffusion of an acid generated from the specified acid generating agent (A1) can be appropriately suppressed, and consequently the LWR of the resist pattern formed from the radiation-sensitive resin composition can be more improved.

The compound represented by the above formula (1) is exemplified by compounds represented by the following formulae (1a-1) to (1a-16), and the like.

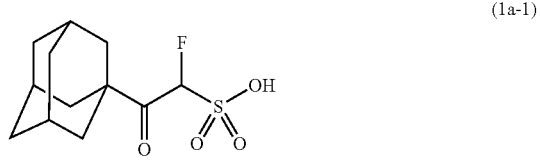
(1a-1)

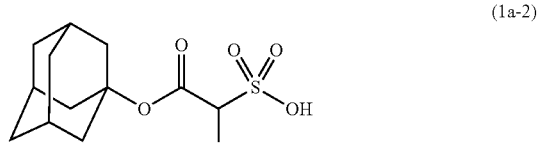
(1a-2)

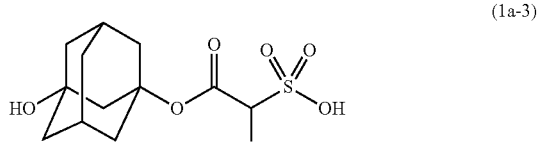
(1a-3)

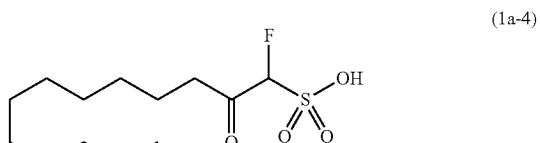
(1a-4)

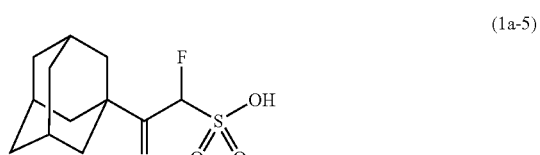
(1a-5)

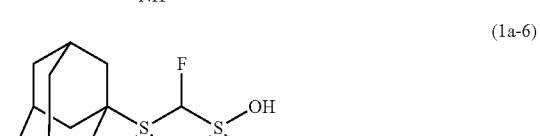
(1a-6)

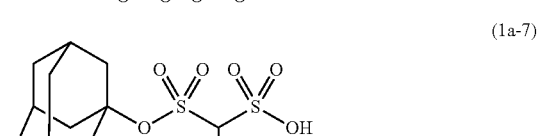
(1a-7)

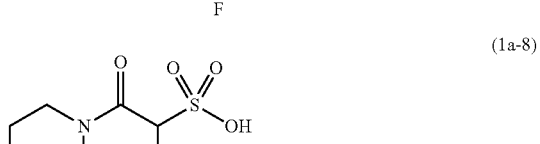
(1a-8)

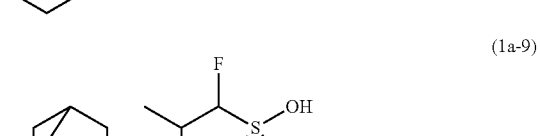
(1a-9)

-continued

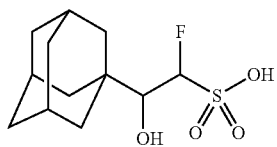
(1a-10)

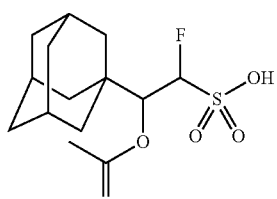
(1a-11)

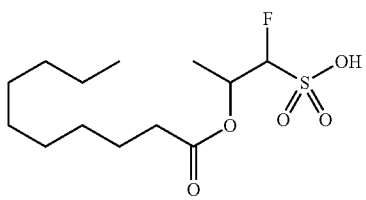
(1a-12)

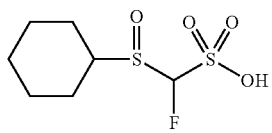
(1a-13)

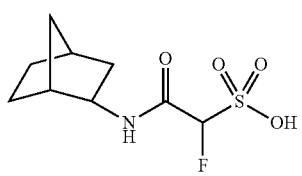
(1a-14)

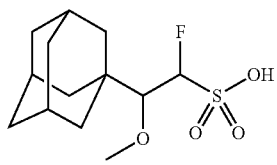
(1a-15)

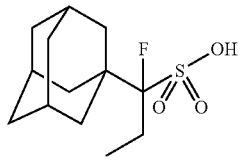
(1a-16)

Of these, the compound represented by the above formula (1) is preferably the compounds represented by the above formulae (1a-1) to (1a-12), more preferably the compounds represented by the above formulae (1a-1) to (1a-4) and the above formula (1a-8), and still more preferably the compounds represented by the above formulae (1a-1) and (1a-2).

The specified acid generating agent (A1) is typically constituted with a cation, and a sulfonate anion generated by removing a proton from a sulfo group of the compound represented by the above formula (1). The cation constituting the specified acid generating agent (A1) is not particularly limited as long as it is a cation which can stably form the specified acid generating agent (A1), and may be either monovalent or polyvalent. Examples of the cation include onium cations such as O, S, Se, N, P, As, Sb, Cl, Br and I. Of these, S and I are preferred. In other words, the specified acid generating agent (A1) is preferably a sulfonium salt compound or an iodonium salt compound. When the specified acid generating agent (A1) is provided in the form of the specified salt compound, radiation sensitivity of the specified acid generating agent (A1) can be more improved.

The monovalent onium cation is exemplified by a cation represented by the following formula (2) as the sulfonium cation, and a cation represented by the formula (3) as the iodonium cation, and the like.

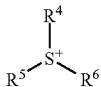
(2)

In the above formula (2), $R^4$, $R^5$ and $R^6$ each independently represent an unsubstituted or optionally substituted linear or branched alkyl group having 1 to 10 carbon atoms, or an unsubstituted or optionally substituted aryl group having 6 to 18 carbon atoms, wherein two or more of $R^4$, $R^5$ and $R^6$ may taken together represent a ring structure by binding with one another together with the sulfur atom to which each bonds.

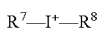
(3)

In the above formula (3), $R^7$ and $R^8$ each independently represent an unsubstituted or optionally substituted linear or branched alkyl group having 1 to 10 carbon atoms, or an unsubstituted or optionally substituted aryl group having 6 to 18 carbon atoms, wherein $R^7$ and $R^8$ may taken together represent a ring structure by binding with each other together with the iodine atom to which each bonds.

The onium cation represented by the above formula (2) is preferably an onium cation represented by the following formulae (2-1) and (2-2). The onium cation represented by the above formula (3) is preferably an onium cation represented by the following formula (3-1).

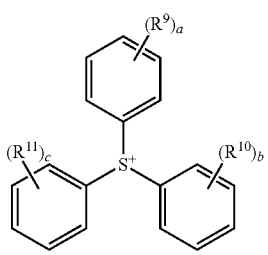
(2-1)

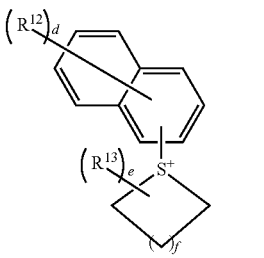
(2-2)

In the above formula (2-1), $R^9$, $R^{10}$ and $R^{11}$ each independently represent a hydroxyl group, a halogen atom, an unsubstituted or optionally substituted linear or branched alkyl group having 1 to 12 carbon atoms, or an unsubstituted or optionally substituted aryl group having 6 to 12 carbon atoms;

and a, b and c are each independently an integer of 0 to 5, wherein provided that $R^9$, $R^{10}$ and $R^{11}$ are each present in a plurality of number, the plurality of $R^9$s, $R^{10}$s and $R^{11}$s may be the same or different and two or more $R^9$, $R^{10}$ and $R^{11}$ may each bind to form a ring structure.

In the above formula (2-2), $R^{12}$ represents an unsubstituted or optionally substituted linear or branched alkyl group having 1 to 8 carbon atoms, or an unsubstituted or an optionally substituted aryl group having 6 to 8 carbon atoms; $R^{13}$ represents an unsubstituted or optionally substituted linear or branched alkyl group having 1 to 7 carbon atoms, or an unsubstituted or optionally substituted aryl group having 6 to 7 carbon atoms; d is an integer of 0 to 7; e is an integer of 0 to 6; f is an integer of 0 to 3, wherein provided that $R^{12}$ and $R^{13}$ are each present in a plurality of number, the plurality of $R^{12}$s and $R^{13}$s may be each the same or different, and two or more $R^{12}$s and $R^{13}$s may each bind to form a ring structure.

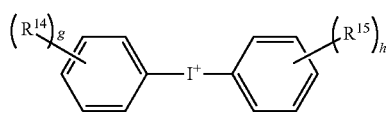

(3-1)

In the above formula (3-1), $R^{14}$ and $R^{15}$ each independently represent a nitro group, a halogen atom, an unsubstituted or optionally substituted linear or branched alkyl group having 1 to 12 carbon atoms, or unsubstituted or optionally substituted aryl group having 6 to 12 carbon atoms; g and h are each independently an integer of 0 to 5, wherein provided that $R^{14}$ and $R^{15}$ are each present in a plurality of number, the plurality of $R^{14}$s and $R^{15}$s may be each the same or different, and two or more $R^{14}$s and $R^{15}$s may each bind to form a ring structure.

Examples of the sulfonium cation include cations represented by the following formulae (i-1) to (i-64), and the like. Examples of the iodonium cation include cations represented by the following formulae (ii-1) to (ii-39), and the like.

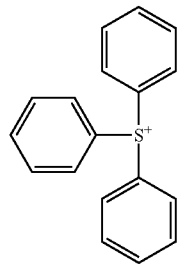

(i-1)

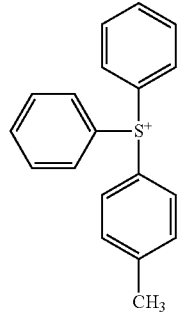

(i-2)

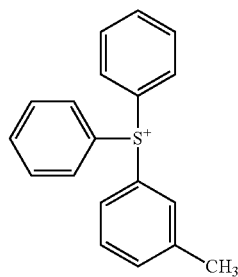

(i-3)

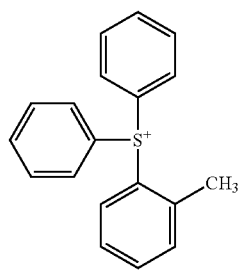

(i-4)

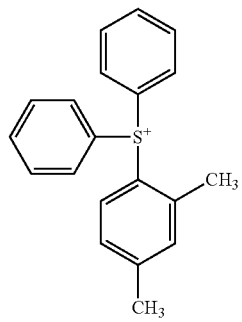

(i-5)

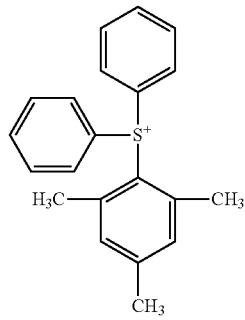

(i-6)

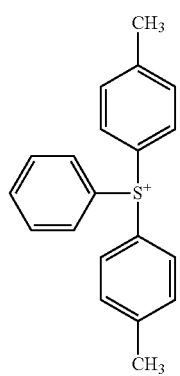

(i-7)

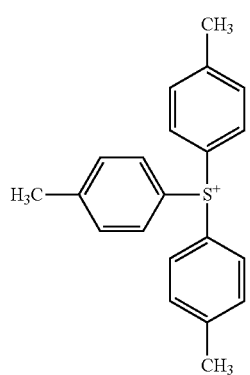
(i-8)
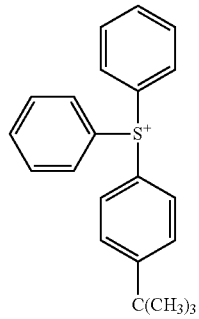
(i-12)
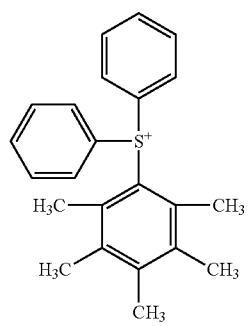
(i-9)
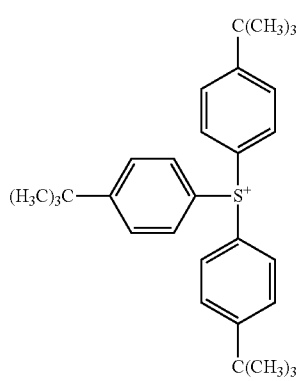
(i-13)
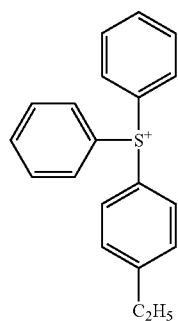
(i-10)
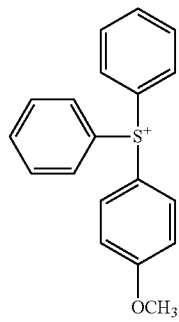
(i-14)
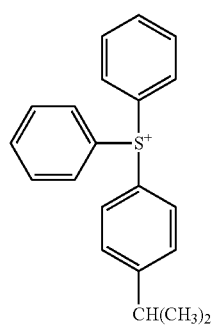
(i-11)
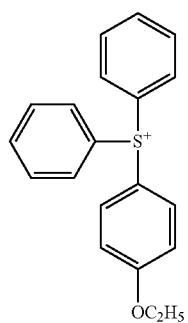
(i-15)

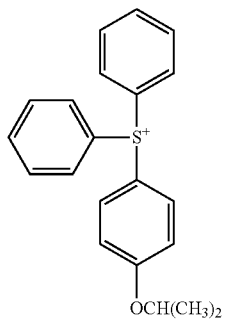
(i-16)
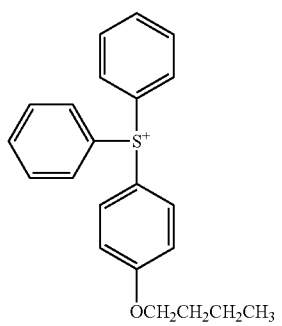
(i-17)
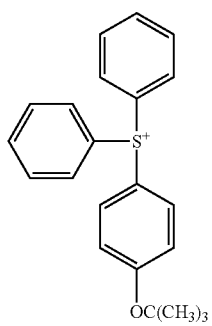
(i-18)
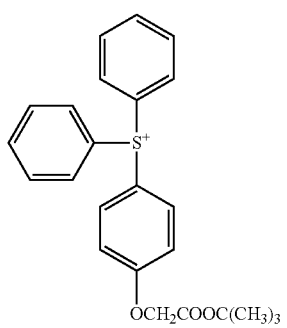
(i-19)
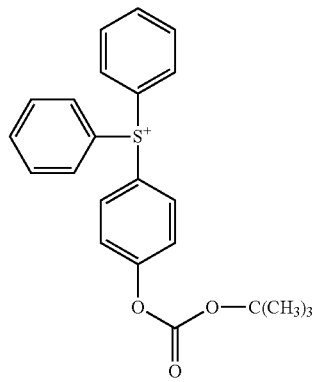
(i-20)
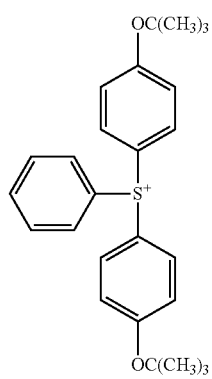
(i-21)
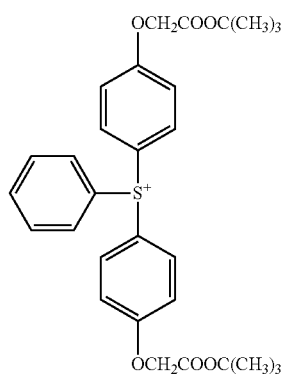
(i-22)
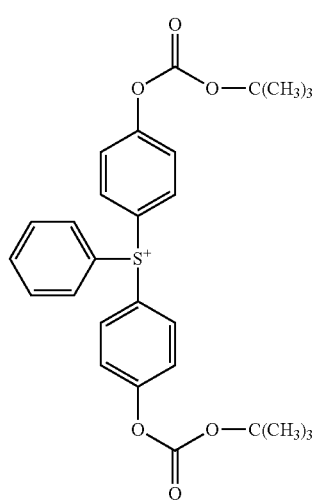
(i-23)

(i-24)
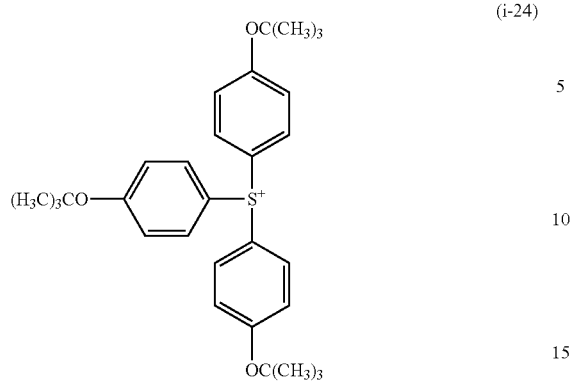
(i-25)
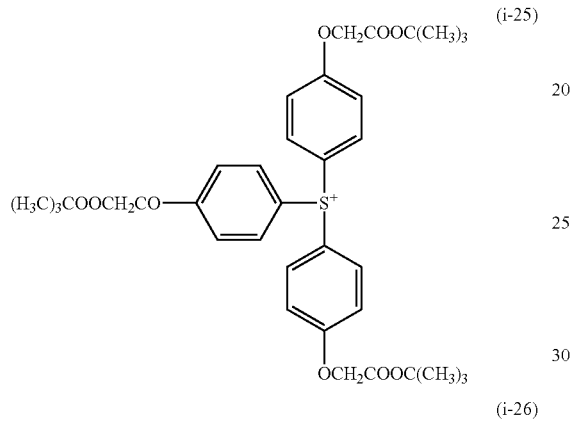
(i-26)
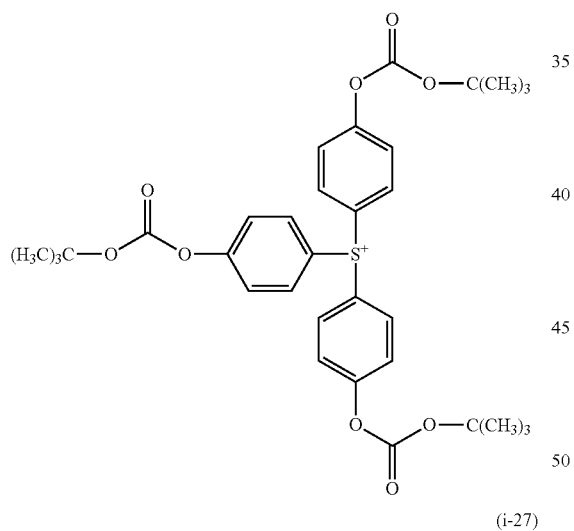
(i-27)
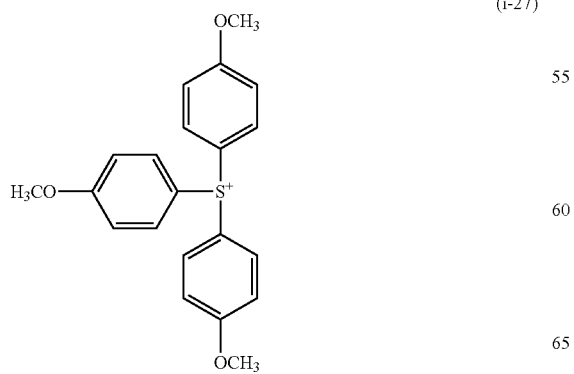
(i-28)
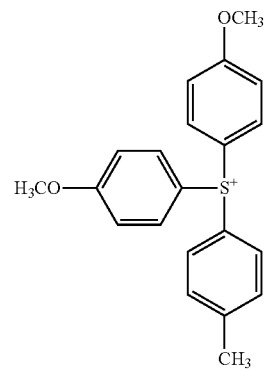
(i-29)
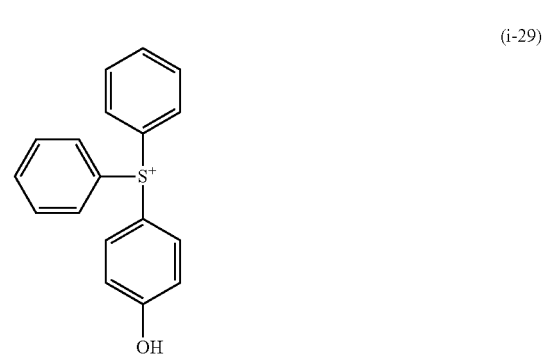
(i-30)
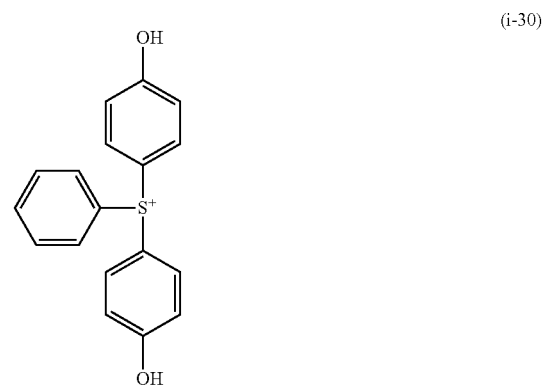
(i-31)
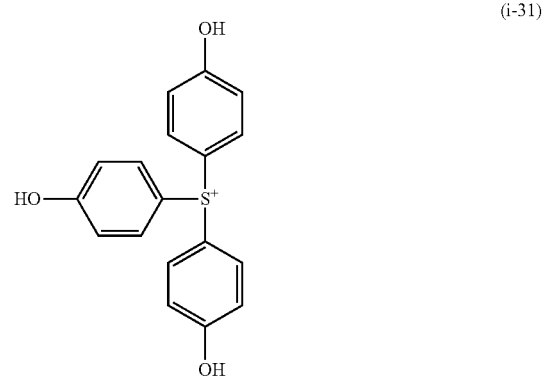

(i-32)
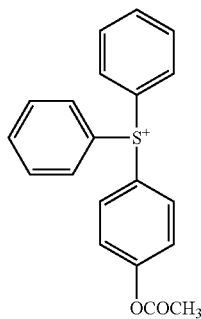
(i-33)
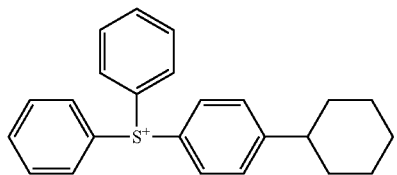
(i-34)
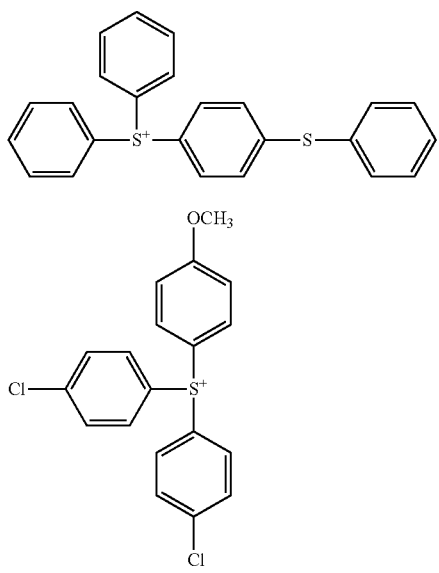
(i-35)
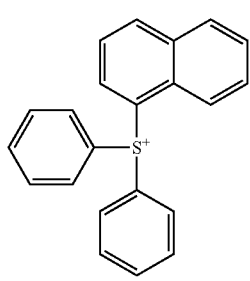
(i-36)
(i-37)
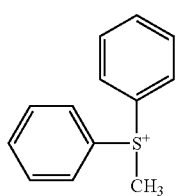
(i-38)
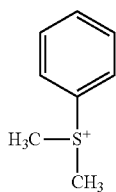
(i-39)
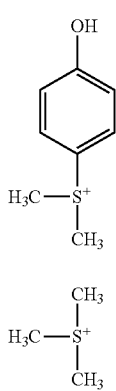
(i-40)
(i-41)
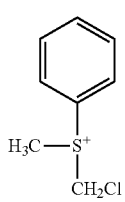
(i-42)
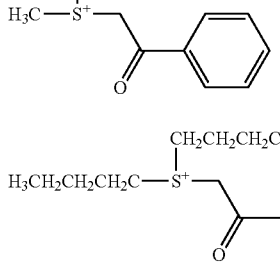
(i-43)
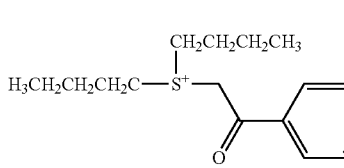
(i-44)
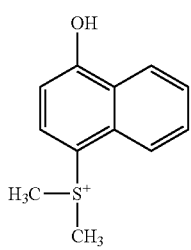
(i-45)
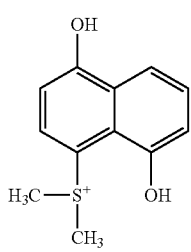

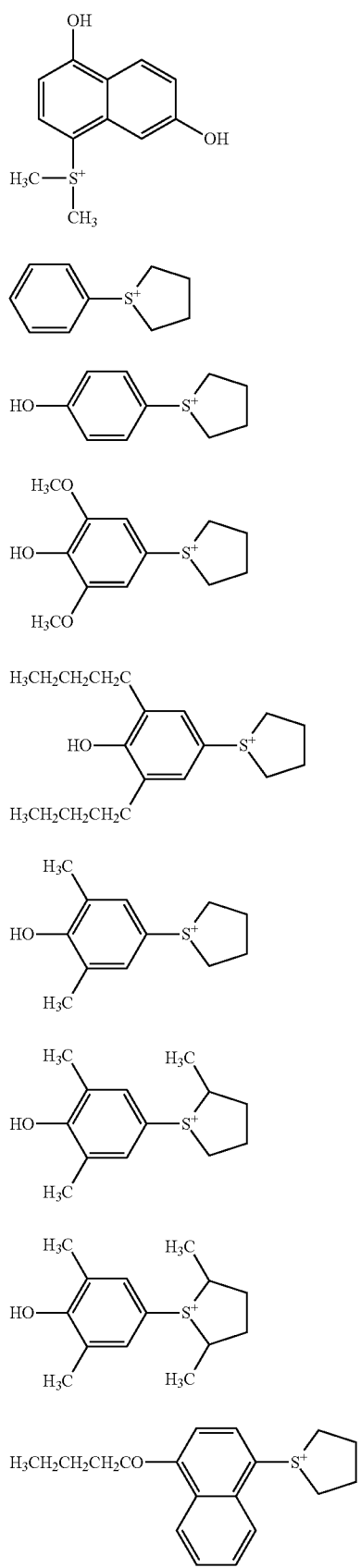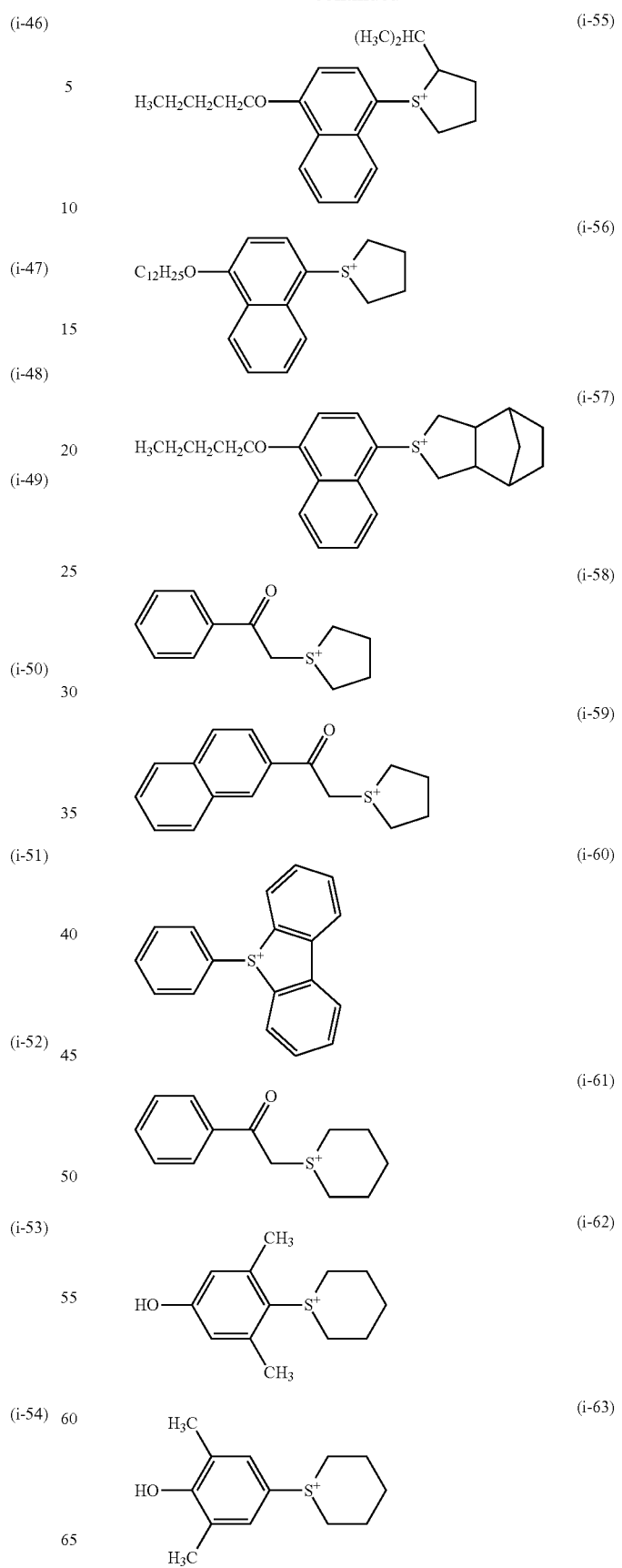

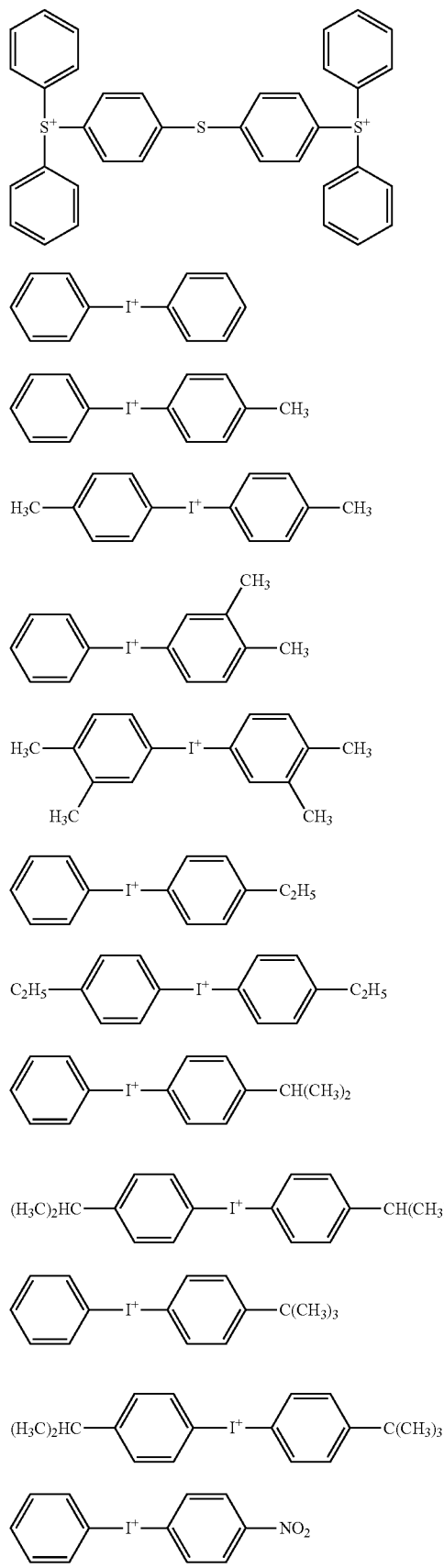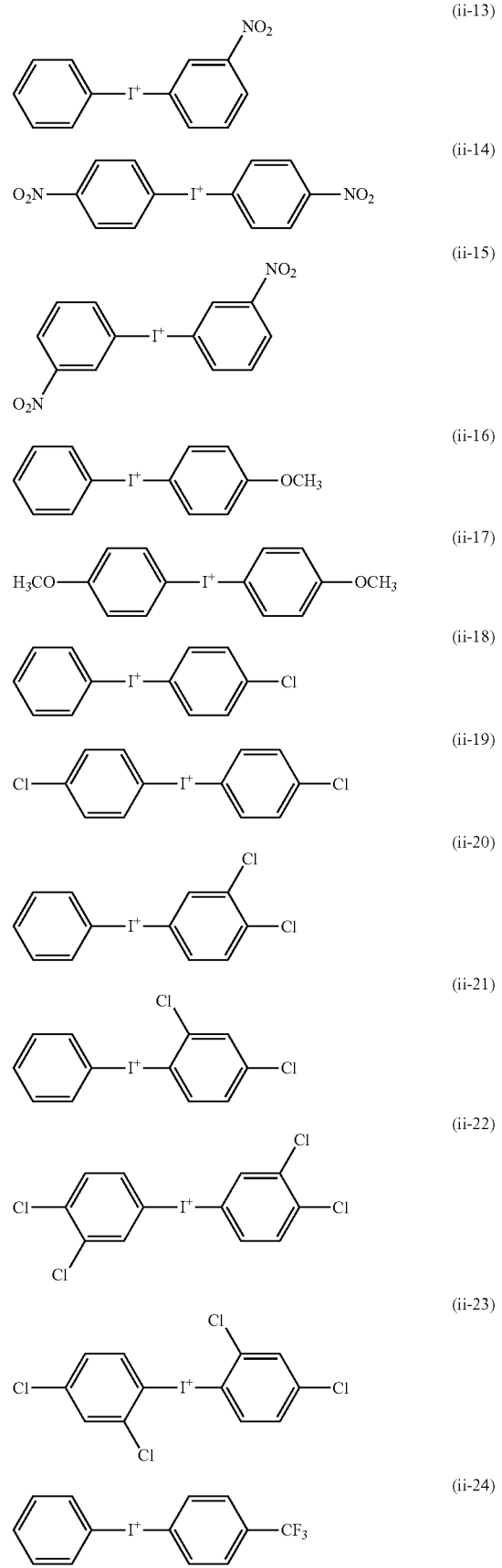

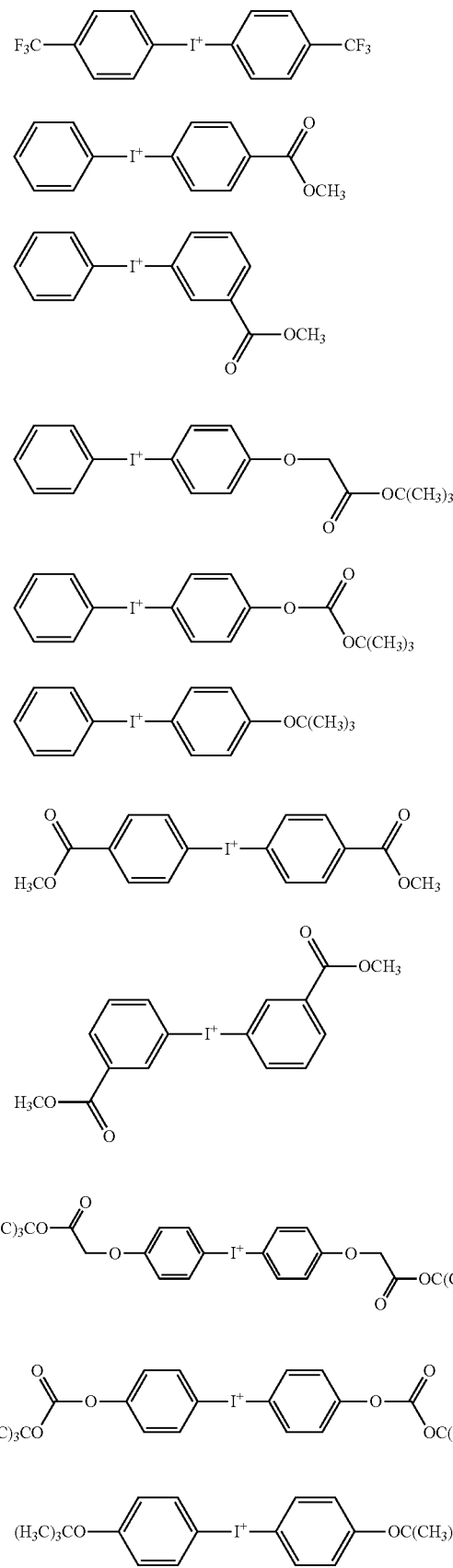
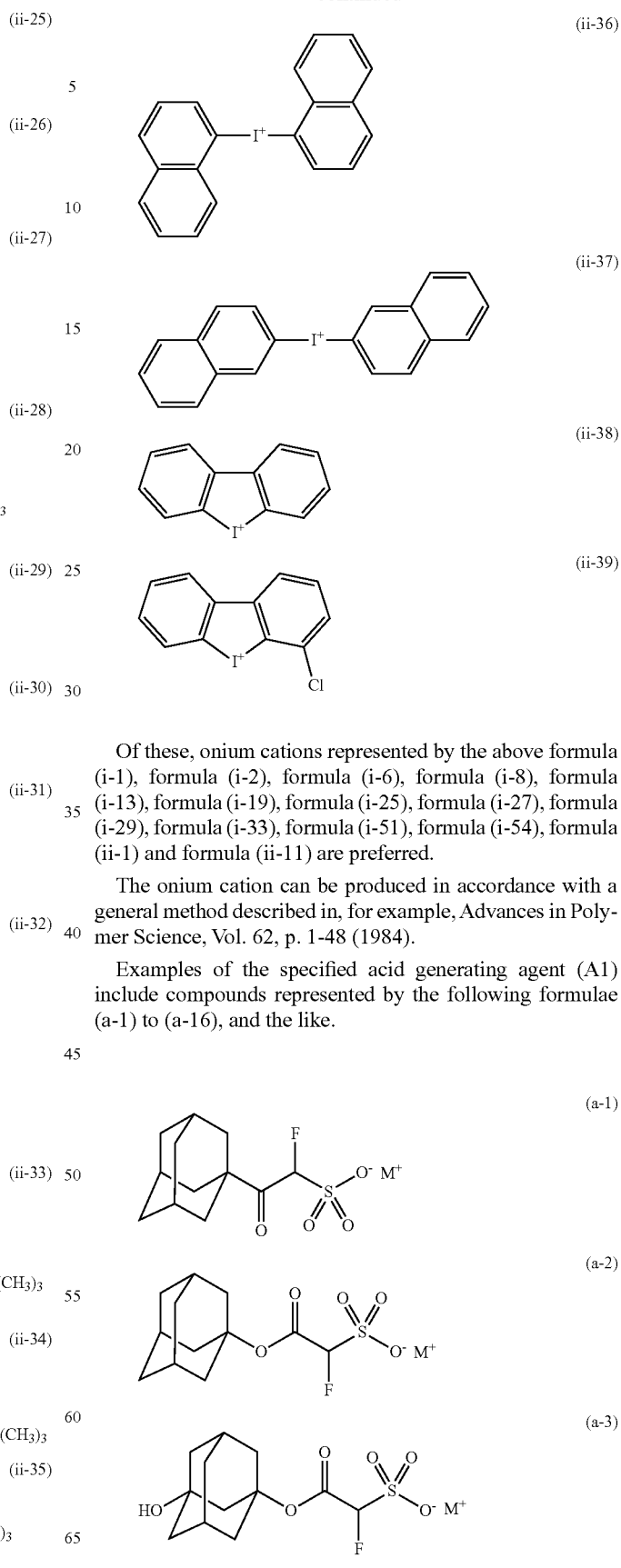

Of these, onium cations represented by the above formula (i-1), formula (i-2), formula (i-6), formula (i-8), formula (i-13), formula (i-19), formula (i-25), formula (i-27), formula (i-29), formula (i-33), formula (i-51), formula (i-54), formula (ii-1) and formula (ii-11) are preferred.

The onium cation can be produced in accordance with a general method described in, for example, Advances in Polymer Science, Vol. 62, p. 1-48 (1984).

Examples of the specified acid generating agent (A1) include compounds represented by the following formulae (a-1) to (a-16), and the like.

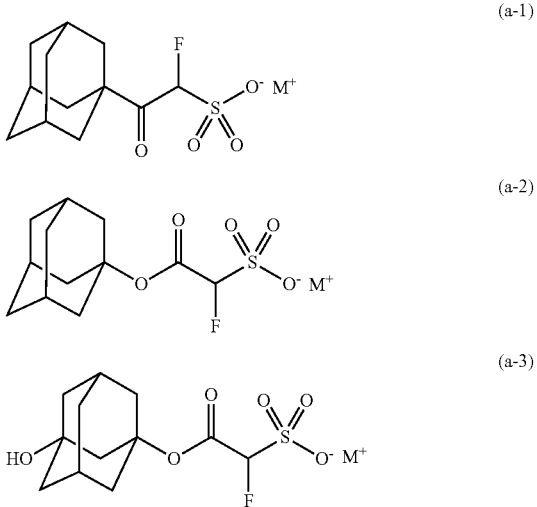

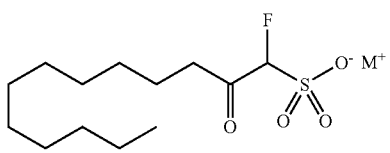
(a-4)

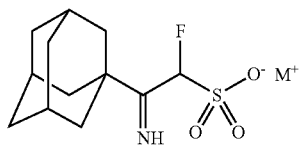
(a-5)

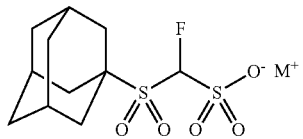
(a-6)

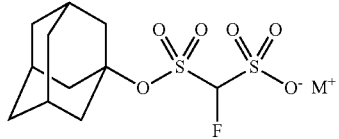
(a-7)

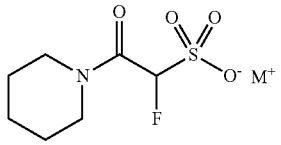
(a-8)

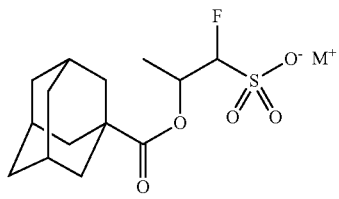
(a-9)

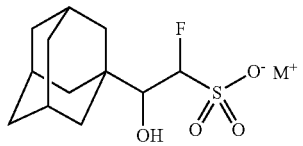
(a-10)

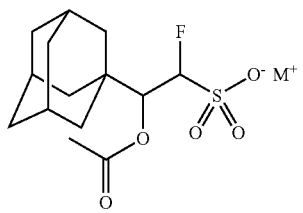
(a-11)

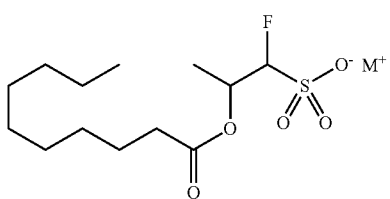
(a-12)

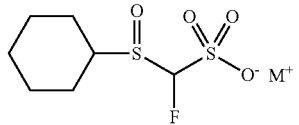
(a-13)

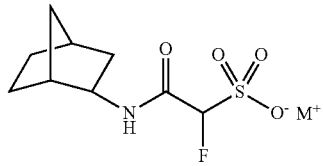
(a-14)

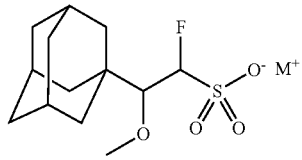
(a-15)

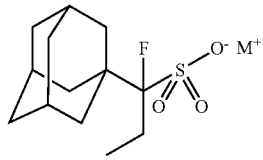
(a-16)

In the above formulae (a-1) to (a-16), $M^+$ represents a monovalent onium cation.

Of these, the specified acid generating agent (A1) is preferably compounds represented by the above formulae (a-1) to (a-12), more preferably compounds represented by the above formulae (a-1) to (a-4) and the compounds represented by the above formula (a-8), and still more preferably compounds represented by the above formulae (a-1) and (a-2).

The specified acid generating agent (A1) may be used in combination of two or more thereof. In addition, the specified acid generating agent (A1) may contain (A2) an acid generating agent other than the specified acid generating agent (A1) (hereinafter, may be also referred to as "acid generating agent (A2)").

The acid generating agent (A2) is preferably a compound represented by the following formula (8):

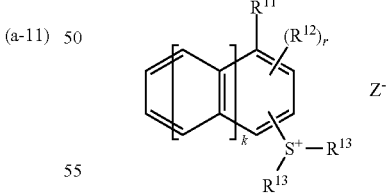
(8)

in the above formula (8), $R^{11}$ represents a hydrogen atom, a fluorine atom, a hydroxyl group, a cyano group, an alkyl group having 1 to 10 carbon atoms, an alkoxy group having 1 to carbon atoms or an alkoxycarbonyl group having 2 to 11 carbon atoms; r is an integer of 0 to 10; $R^{12}$ represents an alkyl group having 1 to 10 carbon atoms, an alkoxy group having 1 to 10 carbon atoms or a (cyclo)alkanesulfonyl group having 1 to 10 carbon atoms, wherein provided that $R^{12}$ is present in a plurality of number, the plurality of $R^{12}$s may be each the same or different; $R^{13}$ each independently represents an alkyl group having 1 to 10 carbon atoms or aryl group, wherein two $R^{13}$s may taken together represent a monovalent group having 2 to 10 carbon atoms together with the sulfur atom to which the $R^{13}$s bond; k is an integer of 0 to 2; $Z^-$ represents $R_{14}C_yF_{2y}SO_3^-$ or $R^{14}SO_3^-$ (wherein, $R^{14}$ represents a hydrogen atom, a fluorine atom or a hydrocarbon group having 1 to 12 carbon atoms; and y is an integer of 1 to 10), or an anion represented by the following formulae:

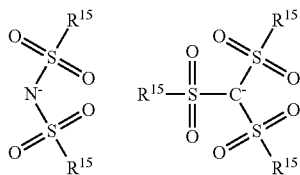

in the above formula, $R^{15}$s each independently represent a fluorinated alkyl group having 1 to 10 carbon atoms, wherein two $R^{15}$s may taken together represent a fluorinated alkylene group having 2 to 10 carbon atoms by binding with each other.

Examples of the alkyl group having 1 to 10 carbon atoms represented by the $R^{11}$, $R^{12}$ and $R^{13}$ include linear alkyl groups such as a methyl group, an ethyl group, a n-propyl group, a n-butyl group, a n-pentyl group, a n-hexyl group, a n-heptyl group, a n-octyl group, a n-nonyl group and a n-decyl group, branched alkyl groups such as a t-butyl group, a neopentyl group, a 2-ethylhexyl group, and the like. Of these, a methyl group, an ethyl group and a n-butyl group, and a t-butyl group are preferred.

Examples of the alkoxy group having 1 to 10 carbon atoms represented by the $R^{11}$ and $R^{12}$ include linear alkoxy groups such as a methoxy group, an ethoxy group, a n-propoxy group and a n-butoxy group, branched alkoxy groups such as an i-propoxy group, a 2-methylpropoxy group, a 1-methylpropoxy group, a t-butoxy group, a neopentyloxy group and a 2-ethylhexyloxy group, and the like. Of these, a methoxy group, an ethoxy group, a n-propoxy group, and a n-butoxy group are preferred.

Examples of the alkoxycarbonyl group having 2 to 11 carbon atoms represented by the $R^{11}$ include linear alkoxycarbonyl groups such as a methoxycarbonyl group, an ethoxycarbonyl group, a n-propoxy carbonyl group, a n-butoxycarbonyl group and a n-pentyloxy carbonyl group, branched alkoxycarbonyl groups such as an i-propoxycarbonyl group, a 2-methylpropoxy carbonyl group, a 1-methylpropoxycarbonyl group, a t-butoxycarbonyl group, a neopentyloxycarbonyl group and a 2-ethylhexyloxycarbonyl group, and the like. Of these, a methoxycarbonyl group, an ethoxycarbonyl group, and a n-butoxycarbonyl group are preferred.

Examples of the (cyclo)alkanesulfonyl group having 1 to 10 carbon atoms represented by the $R^{12}$ include linear alkanesulfonyl groups such as a methanesulfonyl group, an ethanesulfonyl group, a n-propane sulfonyl group, a n-butanesulfonyl group, a n-pentanesulfonyl group and a n-hexanesulfonyl group, branched alkanesulfonyl groups such as a tert-butanesulfonyl group, a neopentane sulfonyl group and a 2-ethylhexanesulfonyl group, cycloalkanesulfonyl groups such as a cyclopentanesulfonyl group and a cyclohexanesulfonyl group, and the like. Of these, a methanesulfonyl group, an ethanesulfonyl group, a n-propanesulfonyl group, a n-butanesulfonyl group, a cyclopentanesulfonyl group, and a cyclohexanesulfonyl group are preferred.

"r" is preferably an integer of 0 to 2.

Examples of the aryl group represented by the $R^{13}$ include a phenyl group and substituted phenyl groups such as an o-tolyl group, a m-tolyl group, a p-tolyl group, a 2,3-dimethyl phenyl group, a 2,4-dimethyl phenyl group, a 2,5-dimethyl phenyl group, a 2,6-dimethyl phenyl group, a 3,4-dimethyl phenyl group, a 3,5-dimethyl phenyl group, a 2,4,6-trimethyl phenyl group, a 4-ethylphenyl group, a 4-t-butylphenyl group, a 4-cyclohexyl phenyl group, a 4-fluorophenyl group, a 4-methoxyphenyl group and a 4-t-butoxyphenyl group, a naphthyl group and substituted naphthyl groups such as a 2-methyl-1-naphthyl group, a 3-methyl-1-naphthyl group, a 4-methyl-1-naphthyl group, a 5-methyl-1-naphthyl group, a 6-methyl-1-naphthyl group, a 7-methyl-1-naphthyl group, a 8-methyl-1-naphthyl group, a 2,3-dimethyl-1-naphthyl group, a 2,4-dimethyl-1-naphthyl group, a 2,5-dimethyl-1-naphthyl group, a 2,6-dimethyl-1-naphthyl group, a 2,7-dimethyl-1-naphthyl group, a 2,8-dimethyl-1-naphthyl group, a 3,4-dimethyl-1-naphthyl group, a 3,5-dimethyl-1-naphthyl group, a 3,6-dimethyl-1-naphthyl group, a 3,7-dimethyl-1-naphthyl group, a 3,8-dimethyl-1-naphthyl group, a 4,5-dimethyl-1-naphthyl group, a 5,8-dimethyl-1-naphthyl group, a 4-ethyl-1-naphthyl group, a 2-naphthyl group, a 1-methyl-2-naphthyl group, a 3-methyl-2-naphthyl group, a 4-methyl-2-naphthyl group, a 1-(4-methoxynaphthyl)group, a 1-(4-ethoxynaphthyl)group, a 1-(4-n-propoxy naphthyl)group, a 1-(4-n-butoxynaphthyl)group, a 2-(7-methoxynaphthyl)group, a 2-(7-ethoxynaphthyl)group, a 2-(7-n-propoxy naphthyl)group and a 2-(7-n-butoxynaphthyl)group, and the like. A part or all hydrogen atoms included in these groups are unsubstituted or optionally substituted by a substituent.

The monovalent group having 2 to 10 carbon atoms which may be taken together represented by the two $R^{13}$s with the sulfur atom to which the $R^{13}$s bond is preferably a group that includes a 5-membered ring or a 6-membered ring, and more preferably a group that includes a tetrahydrothiophene ring. It is to be noted that the monovalent group is unsubstituted or optionally substituted with at least one group selected from the group consisting of a hydroxyl group, a carboxyl group, a cyano group, a nitro group, an alkoxy group, an alkoxyalkyl group, an alkoxycarbonyl group and an alkoxycarbonyloxy group. $R^{13}$ is preferably a methyl group, an ethyl group, a phenyl group, a 4-methoxyphenyl group or a 1-naphthyl group, or a group that includes a tetrahydrothiophene ring represented by the two $R^{13}$s taken together by binding each other together with the sulfur atom to which the $R^{13}$s bond.

The cation in the above formula (8) is preferably a triphenylsulfonium cation, tri-1-naphthylsulfonium cation, a tri(tert-butylphenyl)sulfonium cation, a 4-fluorophenyldiphenylsulfonium cation, a di(4-fluorophenyl)phenylsulfonium cation, a tri(4-fluorophenyl)sulfonium cation, a 4-cyclohexylphenyldiphenylsulfonium cation, a 4-methanesulfonylphenyldiphenylsulfonium cation, a 4-cyclohexanesulfonylphenyldiphenylsulfonium cation, a 1-naphthyldimethylsulfonium cation, a 1-naphthyldiethylsulfonium cation, a 1-(4-hydroxynaphthyl)dimethylsulfonium cation, a 1-(4-methylnaphthyl)dimethylsulfonium cation, a 1-(4-methylnaphthyl)diethylsulfonium cation, a 1-(4-cyanonaphthyl)dimethylsulfonium cation, a 1-(4-cyanonaphthyl)diethylsulfonium cation, a 1-(3,5-dimethyl-4-hydroxyphenyl)tetrahydrothiophenium cation, a 1-(4-methoxynaphthyl)tetrahydrothiophenium cation, a 1-(4-ethoxynaphthyl)tetrahydrothiophenium cation, a 1-(4-n-propoxynaphthyl)tetrahydrothiophenium cation, a 1-(4-n-butoxynaphthyl)tetrahydrothiophenium cation, a 2-(7-methoxynaphthyl)tetrahydrothiophenium cation, a 2-(7-ethoxynaphthyl)tetrahydrothiophenium cation, a 2-(7-n-propoxynaphthyl)tetrahydrothiophenium cation, or a 2-(7-n-butoxynaphthyl)tetrahydrothiophenium cation.

The y is preferably 1, 2, 4 or 8.

The hydrocarbon group having 1 to 12 carbon atoms represented by the $R^{14}$ is preferably an alkyl group having 1 to 12 carbon atoms, a cycloalkyl group having 3 to 12 carbon atoms, and a bridged alicyclic hydrocarbon group having 7 to 12 carbon atoms. Specifically, a methyl group, an ethyl group, n-propyl group, an i-propyl group, a n-butyl group, a 2-methylpropyl group, a 1-methylpropyl group, a t-butyl group, a n-pentyl group, a neopentyl group, a n-hexyl group, a cyclohexyl group, a n-heptyl group, a n-octyl group, a 2-ethylhexyl group, a n-nonyl group, a n-decyl group, a norbornyl group, a norbornylmethyl group, a hydroxynorbornyl group, an adamantyl group, and the like are exemplified.

Examples of the fluorinated alkyl group having 1 to 10 carbon atoms represented by the $R^{15}$ include a trifluoromethyl group, a pentafluoroethyl group, a heptafluoropropyl group, a nonafluorobutyl group, a dodecafluoropentyl group, a perfluorooctyl group, and the like.

Examples of the bivalent fluorinated alkylene group having 2 to 10 carbon atoms which may be represented by two $R^{15}$s taken together by binding each other include a tetrafluoroethylene group, a hexafluoropropylene group, an octafluorobutylene group, a decafluoropentylene group, an undecafluorohexylene group, and the like.

The anion in the above formula (8) is preferably a trifluoromethanesulfonate anion, a perfluoro n-butanesulfonate anion, a perfluoro n-octanesulfonate anion, a 2-(bicyclo[2.2.1]hepta-2-yl)-1,1,2,2-tetrafluoroethanesulfonate anion, a 2-(bicyclo[2.2.1]hepta-2-yl)-1,1-difluoroethanesulfonate anion, a 1-adamantyl sulfonate anion, and anions represented by the following formulae:

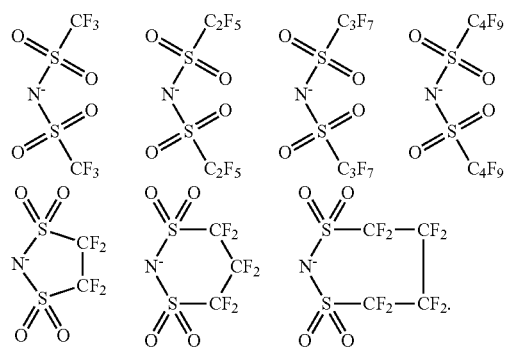

The acid generating agent (A2) may be used as a mixture of two or more types thereof.

When the acid generating agent (A2) is contained, the content of the acid generating agent (A2) is typically 1 part by mass to 95 parts by mass, and preferably 10 parts by mass to 90 parts by mass with respect to 100 parts by mass of the specified acid generating agent (A1).

The content of the specified acid generating agent (A1) is preferably 0.1 parts by mass to 20 parts by mass, and more preferably 1 part by mass to 15 parts by mass with respect to 100 parts by mass of the base polymer (B). When the content of the specified acid generating agent (A1) is less than 0.1 parts by mass, sensitivity or resolution as a resist film may be deteriorated. On the other hand, when the content of the specified acid generating agent (A1) is beyond 20 parts by mass, coating properties and pattern formation properties as a resist film may be deteriorated.

<Synthesis Method of (A1) Specified Acid Generating Agent>

A method for synthesizing the specified acid generating agent (A1) will be explained by way of example, regarding an acid generating agent represented by the following formula:

in the above formula (A-1), $R^2$, $R^3$ and X are as defined in the above formula (1-1); and $Q^+$ represents a monovalent onium cation.

A method for synthesizing the specified acid generating agent (A1) in which the X represents a carbonyl group is explained. This synthesis method includes:

(A) a step of allowing a compound represented by the following formula (1a) to react with a fluorinated alkali metal to obtain a compound represented by the following formula (1b);

(B) a step of allowing a compound represented by the following formula (1b) to react with a brominating agent to obtain a compound represented by the following formula (1c);

(C) a step of allowing a compound represented by the following formula (1c) to react with a diol to obtain a compound represented by the following formula (1d);

(D) a step of allowing a compound represented by the following formula (1d) to react with a sulfinic acid salt, and then with an oxidizing agent to obtain a compound represented by the following formula (1e); and (E) a step of allowing a compound represented by the following formula (1e) to react with an onium salt represented by the following formula (1f) to obtain the compound represented by the above formula (A-1).

Due to the X being a carbonyl group, the reactions in the step (A) and the step (B) can more readily proceed.

In the above formula (1a), $R^2$ and $R^3$ are as defined in the above formula (1-1).

In the above formula (1b), $R^2$ and $R^3$ are as defined in the above formula (1-1).

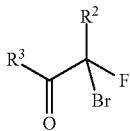
(1c)

In the above formula (1c), $R^2$ and $R^3$ are as defined in the above formula (1-1).

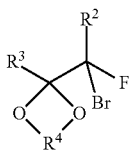
(1d)

In the above formula (1d), $R^2$ and $R^3$ are as defined in the above formula (1-1); and $R^4$ represents a bivalent organic group.

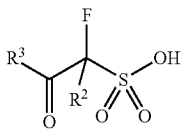
(1e)

In the above formula (1e), $R^2$ and $R^3$ are as defined in the above formula (1-1).

$$Q^+Z^- \quad (1f)$$

In the above formula (1f), $Q^+$ is as defined in the above formula (A-1); and $Z^-$ represents a monovalent anion.

The fluorinated alkali metal used in the step (A) is exemplified by potassium fluoride, sodium fluoride, and the like. The amount of the fluorinated alkali metal used is preferably 1 mol to 20 mol, and more preferably 2 mol to 10 mol per mol of the compound represented by the above formula (1a). Moreover, the step (A) is preferably carried out in the presence of a solvent. The solvent which may be used is typically a hydrocarbon solvent, and preferably an aromatic hydrocarbon solvent such as benzene, toluene or xylene.

The step (A) is preferably carried out in the presence of a phase-transfer catalyst. The phase-transfer catalyst is exemplified by crown ethers such as 24-crown-8, 18-crown-6, 15-crown-5, 12-crown-4, benzo-18-crown-6, benzo-15-crown-5, benzo-12-crown-4, dibenzo-30-crown-10, dibenzo-24-crown-8, dibenzo-21-crown-7, dibenzo-18-crown-6, dicyclohexano-24-crown-8, dicyclohexano-18-crown-6 and N,N'-dibenzyl-4,13-diaza-18-crown-6. The reaction temperature is typically 0° C. to 200° C., and preferably 20° C. to 150° C. The reaction pressure is typically $1\times10^4$ N/m² to $10^6$ N/m², and preferably an ambient pressure. The reaction time period is typically 0.1 hrs to 100 hrs, and preferably 0.5 hrs to 20 hrs.

The brominating agent which may be used in the step (B) is exemplified by pyridiniumbromide perbromide, and the like. The amount of the brominating agent used is preferably 1 mol to 20 mol, and more preferably 1 mol to 5 mol per mol of the compound represented by the above formula (1b). Moreover, this step is preferably carried out in the presence of a solvent. The solvent is preferably an ether solvent such as diethyl ether, tetrahydrofuran, diisopropyl ether, dioxane, diglyme or dimethoxy ethane. The reaction temperature is typically 0° C. to 200° C., and preferably 10° C. to 100° C. The reaction pressure is typically $1\times10^4$ N/m² to $10^6$ N/m², and preferably an ambient pressure. The reaction time period is typically 0.1 hrs to 100 hrs, and preferably 0.5 hrs to 20 hrs.

A diol which may be used in the step (C) is exemplified by ethylene glycol, propylene glycol, diethylene glycol, and the like. The amount of the diol used is preferably 1 mol to 20 mol, and more preferably 2 mol to 10 mol per mol of the compound represented by the above formula (1c). Moreover, this step is preferably carried out in the presence of a solvent. The solvent which may be used is typically a hydrocarbon solvent, and preferably, an aromatic hydrocarbon solvent such as benzene, toluene or xylene. Furthermore, this step is preferably carried out in the presence of an acid catalyst. The acid catalyst is exemplified by conc. sulfuric acid, p-toluenesulfonic acid, xylene sulfonic acid, and the like. The reaction temperature is typically 0° C. to 200° C., and preferably 20° C. to 150° C. The reaction pressure is typically $1\times10^4$ N/m² to $10^6$ N/m², and preferably an ambient pressure. The reaction time period is typically 0.1 hrs to 100 hrs, and preferably 0.5 hrs to 20 hrs.

The sulfinic acid salt which may be used in the step (D) is exemplified by sodium sulfate, potassium sulfate, and the like. The amount of the sulfinic acid salt used is preferably 1 mol to 20 mol, and more preferably 1 mol to 5 mol per mol of the compound represented by the above formula (1d). Moreover, the reaction with the sulfinic acid salt is carried out preferably in a mixed solvent of an organic solvent with water. The organic solvent is, for example, preferably a solvent having favorable miscibility with water such as lower alcohols, tetrahydrofuran, N,N-dimethylformamide, N,N-dimethylacetamide, acetonitrile and dimethylsulfoxide, more preferably N,N-dimethylacetamide, acetonitrile and dimethylsulfoxide, and particularly preferably acetonitrile. The proportion of the organic solvent used is typically no less than 5 parts by mass, preferably no less than 10 parts by mass, and more preferably no less than 20 parts by mass and no greater than 90 parts by mass with respect to 100 parts by mass of the total of the organic solvent and water.

The reaction is carried out with the sulfinic acid salt preferably under a basic condition. For carrying out the reaction under a basic condition, sodium bicarbonate, potassium bicarbonate or the like may be used. The reaction temperature during allowing to react with the sulfinic acid salt is typically 0° C. to 200° C., and preferably 20° C. to 150° C. The reaction pressure is typically $1\times10^4$ N/m² to $10^6$ N/m², and preferably an ambient pressure. The reaction time period is typically 0.1 hrs to 100 hrs, and preferably 0.5 hrs to 20 hrs.

The oxidizing agent which may be used in the step (D) is exemplified by hydrogen peroxide, m-chloroperbenzoic acid, t-butylhydroperoxide, and the like. The amount of the oxidizing agent used is preferably 1 mol to 20 mol, and more preferably 1 mol to 5 mol per mol of the compound represented by the above formula (1d). Furthermore, a transition metal catalyst may be used in combination together with the oxidizing agent. Examples of the transition metal catalyst include disodium tungstate, iron(III) chloride, ruthenium(III) chloride, selenium(IV) oxide, and the like. The reaction temperature during allowing to react with the oxidizing agent is typically 0° C. to 200° C., and preferably 20° C. to 150° C. The reaction pressure is typically $1\times10^4$ N/m² to $10^6$ N/m², and preferably an ambient pressure. The reaction time period is typically 0.1 hrs to 100 hrs, and preferably 0.5 hrs to 20 hrs.

Examples of the monovalent anion represented by the $Z^-$ include $Cl^-$, $Br^-$, $HSO_4^-$, $H_2PO_4^-$, $BF_4^-$, an aliphatic sulfonate anion, and the like.

The step (E) is typically carried out in a reaction solvent. The reaction solvent is preferably water, an organic solvent such as a lower alcohol, tetrahydrofuran, N,N-dimethylformamide, N,N-dimethylacetamide, acetonitrile or dimethylsulfoxide, more preferably water, methanol, N,N-dimethylacetamide, acetonitrile or dimethylsulfoxide, and particularly preferably water. In addition, water and an organic solvent may be used in combination as needed, the proportion of the organic solvent used in this case is typically no less than 5 parts by mass, preferably no less than 10 parts by mass, and more preferably 20 parts by mass to 90 parts by mass with respect to 100 parts by mass of the total of water and the organic solvent. The amount of the reaction solvent used typically 1 part by mass to 100 parts by mass, preferably 2 parts by mass to 100 parts by mass, and particularly preferably 5 parts by mass to 50 parts by mass per part by mass of the counter ion exchange precursor (compound represented by the above formula (1e)). The reaction temperature is typically 0° C. to 80° C., and preferably 5° C. to 30° C. The reaction time period is typically 0.1 hrs to 16 hrs, and preferably 0.5 hrs to 6 hrs.

A method for synthesizing the specified acid generating agent (A1) when X in the above formula (A-1) represents a —CONH—, —COO—, —SO— or —$SO_2$— group will be explained. Specifically, the method includes (F) a step of allowing a compound represented by the following formula (1g) to react with the sulfinic acid salt, followed by allowing to react with an oxidizing agent to obtain the compound represented by the above formula (1h), and (G) a step of allowing a compound represented by the following formula (1h) to react with the onium salt represented by the above formula (1f) to obtain the compound represented by the above formula (A-1). The step (F) and the step (G) can be carried out similarly to the step (D) and the step (E), respectively. Also in the case in which X in the above formula (A-1) represents the above group, the reactions in the step (A) and the step (B) can readily proceed.

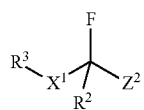

(1g)

In the above formula (1g), $R^2$ and $R^3$ are as defined in the above formula (1-1); $X^1$ represents a —CONH—, —COO-, —SO— or —$SO_2$— group; and $Z^2$ represents Br or Cl.

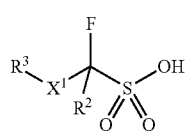

(1h)

In the above formula (1h), $R^2$ and $R^3$ are as defined in the above formula (1-1); and $X^1$ is as defined in the above formula (1g).

<(B) Base Polymer>

The radiation-sensitive resin composition preferably contains the base polymer (B). The base polymer (B) is a component that serves as a base resin of the radiation-sensitive resin composition. The base polymer (B) is exemplified by a polymer which is insoluble or hardly soluble in an alkali and has an acid-dissociable group and which becomes easily soluble in alkali when the acid-dissociable group dissociates (hereinafter, may also be referred to as "(B1) acid-dissociable group-containing polymer"); and a polymer which has one or more types of functional group(s) that exhibits an affinity to an alkaline developer typified by an oxygen-containing functional group such as a phenolic hydroxyl group, an alcoholic hydroxyl group or a carboxyl group and which is soluble in an alkaline developer (hereinafter, may also be referred to as "(B2) alkali-soluble polymer"), and the like.

The radiation-sensitive resin composition containing the acid-dissociable group-containing polymer (B1) can be suitably used as a positive type radiation-sensitive resin composition. The radiation-sensitive resin composition containing the alkali-soluble polymer (B2) can be suitably used as a negative radiation-sensitive resin composition.

Also, when the radiation-sensitive resin composition contains the base polymer (B) together with (C) a fluorine atom-containing polymer described later, the content of the fluorine atom(s) in the base polymer (B) is preferably less than the content of the fluorine atom(s) in the fluorine atom-containing polymer (C). The fluorine atom content in the base polymer (B) is typically less than 10% by mass, and preferably 0% by mass to 6% by mass with respect to 100% by mass of the total of the polymer (B). It is to be noted that herein the fluorine atom content can be calculated from the structure of the polymer determined using $^{13}$C-NMR.

When a resist film is formed using a radiation-sensitive resin composition containing the base polymer (B) and the fluorine atom-containing polymer (C), the distribution of the fluorine atom-containing polymer (C) on the surface of the resist film tends to be high due to hydrophobicity of the fluorine atom-containing polymer (C). In other words, the fluorine atom-containing polymer (C) unevenly distributes on the surface layer of the resist film. Therefore, there is no need to separately form an upper layer film for the purpose of blocking a resist film from a liquid for immersion lithography, and thus the radiation-sensitive resin composition can be suitably used in a liquid immersion lithography process.

[(B1) Acid-Dissociable Group-Containing Polymer]

The acid-dissociable group-containing polymer (B1) is a polymer having an acid-dissociable group in a main chain, a side chain or both the main chain and the side chain. Of these, a polymer having an acid-dissociable group in the side chain is preferable.

The acid-dissociable group-containing polymer (B1) includes (b1) a structural unit having an acid-dissociable group. In addition, the acid-dissociable group-containing polymer (B1) may also include other structural unit as long as effects as (b2) a structural unit having a lactone skeleton and the base polymer (B) are not impaired. It is to be noted that the acid-dissociable group-containing polymer (B1) may include at least two types of each structural unit. Hereinafter, each structural unit will be explained in detail.

(Structure Unit (b1))

The structural unit (b1) is exemplified by a structural unit represented by the following formula (4), and the like.

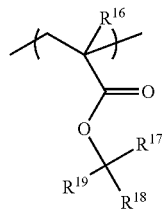

(4)

In the above formula (4), $R^{16}$ represents a hydrogen atom, a methyl group, a trifluoromethyl group or a hydroxymethyl group; and $R^{17}$, $R^{18}$ and $R^{19}$ each independently represent an alkyl group having 1 to 4 carbon atoms or an alicyclic hydrocarbon group having 4 to 20 carbon atoms, and $R^{18}$ and $R^{19}$ may taken together represent a bivalent alicyclic hydrocarbon group having 4 to 20 carbon atoms by binding with each other together with the carbon atom to which the $R^{18}$ and $R^{19}$ bond.

The structural unit (b1) is preferably a structural unit represented by the following formulae (4-1) and (4-2).

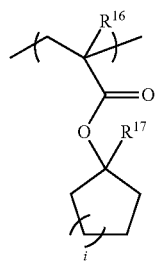

(4-1)

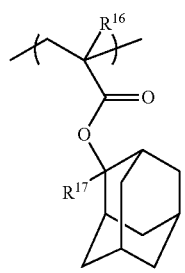

(4-2)

In the above formulae (4-1) and (4-2), $R^{16}$ is as defined in the formula (4); $R^{17}$ each independently represents a linear or branched alkyl group having 1 to 4 carbon atoms; and i is an integer of 1 to 10.

Examples of the linear or branched alkyl group having 1 to 4 carbon atoms represented by the $R^{17}$ include a methyl group, an ethyl group, a n-propyl group, an isopropyl group, a n-butyl group, a 2-methylpropyl group, a 1-methylpropyl group, a tert-butyl group, and the like.

The monomer that gives the structural unit (b1) is preferably (meth)acrylic acid 1-methyl-1-cyclopentyl ester, (meth)acrylic acid 1-ethyl-1-cyclopentyl ester, (meth)acrylic acid 1-isopropyl-1-cyclopentyl ester, (meth)acrylic acid 1-methyl-1-cyclohexyl ester, (meth)acrylic acid 1-ethyl-1-cyclohexyl ester and (meth)acrylic acid 1-ethyl-1-cyclooctyl ester, and (meth)acrylic acid 2-methyl-2-adamantyl ester.

The proportion of the structural unit (b1) contained in the acid-dissociable group-containing polymer (B1) is preferably 5 mol % to 85 mol %, more preferably 10 mol % to 70 mol % and particularly preferably 15 mol % to 60 mol % with respect to the total of the structural units. When the proportion of the structural unit (b1) contained is less than 5 mol %, developability and exposure latitude of the radiation-sensitive resin composition may be deteriorated. To the contrary, when the proportion of the structural unit (b1) contained exceeds 85 mol %, solubility of the acid-dissociable group-containing polymer (B1) into a solvent, and the resolution of the radiation-sensitive resin composition may be deteriorated.

(Structure Unit (b2))

The structural unit (b2) is exemplified by structural units represented by the following formulae, and the like.

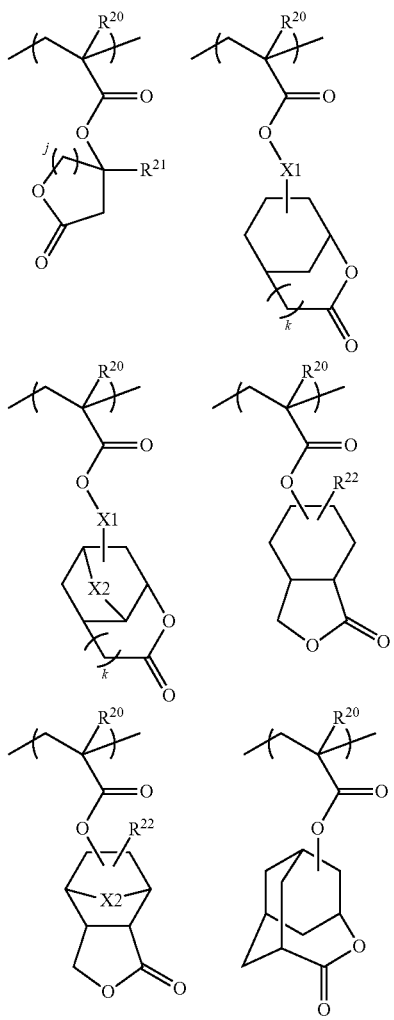

In the above formulae, $R^{20}$ each independently represents a hydrogen atom or a methyl group; $R^{21}$ represents a hydrogen atom, or an unsubstituted or optionally substituted alkyl group having 1 to 4 carbon atoms; $R^{22}$ each independently represents a hydrogen atom or a methoxy group; X1 represents a single bond or a bivalent linking group; X2 represents an oxygen atom or a methylene group; j is an integer of 1 to 3; and k is 0 or 1.

Examples of the alkyl group having 1 to 4 carbon atoms represented by the $R^{21}$ include a methyl group, an ethyl group, a n-propyl group, an isopropyl group, a n-butyl group, a 2-methylpropyl group, a 1-methylpropyl group, tert-butyl group, and the like. Examples of the substituent of the optionally substituted alkyl group having 1 to 4 carbon atoms represented by the $R^{21}$ include a halogen atom (fluorine atom, chlorine atom, bromine atom, etc.), a phenyl group, an acetoxy group, an alkoxy group, and the like.

In the case in which the acid-dissociable group-containing polymer (B1) includes the structural unit (b2), the proportion of the structural unit (b2) contained is preferably 10 mol % to 70 mol %, more preferably 15 mol % to 60 mol % and particularly preferably 20 mol % to 50 mol % with respect to the total of the structural units. When the proportion of the structural unit (b2) contained is less than 10 mol %, resolution as a resist may be decreased. To the contrary, when the proportion of the structural unit (b2) contained exceeds 70 mol %, developability and exposure latitude may be deteriorated.

(Other Structure Unit)

The acid-dissociable group-containing polymer (B1) may include other structural unit except for the structural unit (b1) and the structural unit (b2). Examples of the other structural unit include structural units having a hydroxyalkyl (meth)acrylate such as 2-hydroxyethyl(meth)acrylate, 2-hydroxypropyl(meth)acrylate, 3-hydroxypropyl(meth)acrylate or 2-hydroxyadamantyl(meth)acrylate; structural units having alkali-solubility described later; structural units having a cyclic carbonate structure; structural units having an alicyclic structure described in WO2007/116664, and the like.

The weight average molecular weight (Mw) of the acid-dissociable group-containing polymer (B1) is preferably 1,000 to 50,000, more preferably 1,000 to 40,000, particularly preferably 1,000 to 30,000 in terms of the polystyrene equivalent on gel permeation chromatography (GPC). When the Mw falls within the above range, coating properties of the radiation-sensitive resin composition and suppressive properties of development defects can be improved. When the Mw is less than 1,000, a resist film having sufficient heat resistance may not be obtained. To the contrary, when the Mw exceeds 50,000, developability in a photoresist film may be decreased. The Mw as referred to herein means a measurement value obtained by GPC using GPC columns (manufactured by Tosoh Corporation, G2000HXL×2, G2000HXL×2, G3000HXL×1) under an analytical condition involving a flow rate of 1.0 ml/min, an elution solvent of tetrahydrofuran, a column temperature of 40° C., with monodisperse polystyrene as a standard.

The ratio (Mw/Mn) of the number average molecular weight (Mn) in terms of the polystyrene equivalent on GPC to the Mw is preferably 1 to 5 and more preferably 1 to 4.

[(B2) Alkali-Soluble Polymer]

The alkali-soluble polymer (B2) has at least one type of structural unit (b3) selected from the group consisting of, for example, structural units represented by the following formula, respectively.

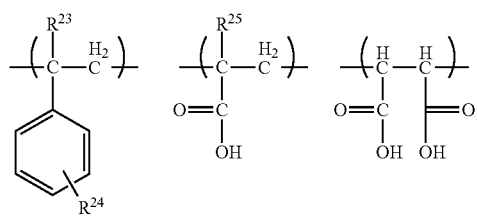

In the above formulae, $R^{23}$ and $R^{25}$ each independently represent a hydrogen atom or a methyl group; $R^{24}$ represents a hydroxyl group, a carboxyl group, —$(CH_2)_m$—COOH, —O—$(CH_2)_m$—COOH, —OCO—$(CH_2)_m$—COOH or —COO—$(CH_2)_m$—COOH; and m is an integer of 1 to 4.

The proportion of the structural unit (b3) contained in the alkali-soluble polymer (B2) is preferably 10 mol % to 100 mol %, and more preferably 20 mol % to 100 mol % with respect to the total of the structural units constituting the alkali-soluble polymer (B2).

The alkali-soluble polymer (B2) may have in addition to the structural unit (b3) at least one "other structural unit" described above. The alkali-soluble polymer (B2) may include two or more types of each structural unit.

The alkali-soluble polymer (B2) is preferably a polymer having poly(4-hydroxystyrene), a 4-hydroxystyrene/4-hydroxy-α-methylstyrene copolymer or a 4-hydroxystyrene/styrene copolymer as a principal component.

The Mw of the alkali-soluble polymer (B2) is typically 1,000 to 150,000, and preferably 3,000 to 100,000.

<Synthesis Method of (B) Base Polymer>

The base polymer (B) can be synthesized by polymerizing a monomer that gives each structural unit, for example, in the presence of a chain transfer agent in a solvent to which a radical polymerization initiator was added.

Examples of the solvent include alkanes such as n-butane, n-pentane, n-hexane, n-heptane, n-octane, n-nonane and n-decane; monocyclic cycloalkanes such as cyclohexane, cycloheptane and cyclooctane; polycyclic cycloalkanes such as decalin and norbornane; aromatic hydrocarbons such as benzene, toluene, xylene, ethylbenzene and cumene; halogenated hydrocarbons such as chlorobutane, bromohexane, dichloroethane, hexamethylene dibromide and chlorobenzene; saturated carboxylate esters such as ethyl acetate, n-butyl acetate, isobutyl acetate and methyl propionate; ketones such as acetone, 2-butanone, 4-methyl-2-pentanone and 2-heptanone; ethers such as tetrahydrofuran, dimethoxyethane and diethoxyethane; alcohols such as methanol, ethanol, 1-propanol, 2-propanol and 4-methyl-2-pentanol, and the like. These solvents may be used either alone, or in combination of two or more thereof.

The polymerization temperature is preferably 40° C. to 150° C. and more preferably 50° C. to 120° C. The reaction time is preferably 1 hour to 48 hrs and more preferably 1 hour to 24 hrs. It is to be noted that the content of impurities such as halogens and metals in the base polymer (B1) is more favorably as low as possible. When the content of impurities is lower, sensitivity, resolution, process stability, pattern configuration, and the like of a resist film can be further enhanced. Purification methods of the base polymer (B1) are exemplified by chemical purification methods such as washing with water and liquid-liquid extraction, combination methods of the chemical purification methods with physical purification methods such as ultrafiltration and centrifugal separation, and the like.

Examples of the solvent used for liquid-liquid extraction include alkanes such as n-pentane, n-hexane, n-heptane, n-octane, n-nonane and n-decane; alcohols such as methanol, ethanol, 1-propanol, 2-propanol and 4-methyl-2-pentanol; ketones such as acetone, 2-butanone, 4-methyl-2-pentanone and 2-heptanone. Of these, n-hexane, n-heptane, methanol, ethanol, acetone and 2-butanone are preferable.

<(C) Fluorine Atom-Containing Polymer>

The fluorine atom-containing polymer (C) that can be suitably contained in the radiation-sensitive composition is a polymer having fluorine atom(s) in a main chain, a side chain, or a main chain and a side chain thereof. Due to the radiation-sensitive containing the fluorine atom-containing polymer (C), a layer having water repellency is formed in the vicinity of the surface of the photoresist film. Therefore, elution of the specified acid generating agent (A1) and (D) an acid diffusion control agent described later, etc., into a liquid for immersion lithography can be suppressed. In addition, due to an increase in a receding contact angle between the resist film and a liquid for immersion lithography, water droplets derived from the liquid for immersion lithography are less likely to remain on the resist film, thereby resulting in prevention of defects caused by the liquid for immersion lithography from occurring.

The fluorine atom-containing polymer (C) preferably includes (c1) a structural unit having a fluorine atom. Also, the fluorine atom-containing polymer (C) may include a structural unit other than the structural unit (c1) as long as the effects of the present invention are not impaired and characteristics as the fluorine atom-containing polymer (C) are provided. Such a structural unit is exemplified by (c2) a structural unit having an acid-dissociable group. It is to be noted that the fluorine atom-containing polymer (C) may include two or more types of each structural unit. Each structural unit will be explained in detail below.

[Structural Unit (c1)]

The structural unit (c1) is not particularly limited as long as it has fluorine atom(s) and is preferably structural units represented by the following formulae (c1-1) to (c1-3). Hereinafter, each structural unit is referred to as (c1-1) a structural unit, (c1-2) a structural unit and (c1-3) a structural unit.

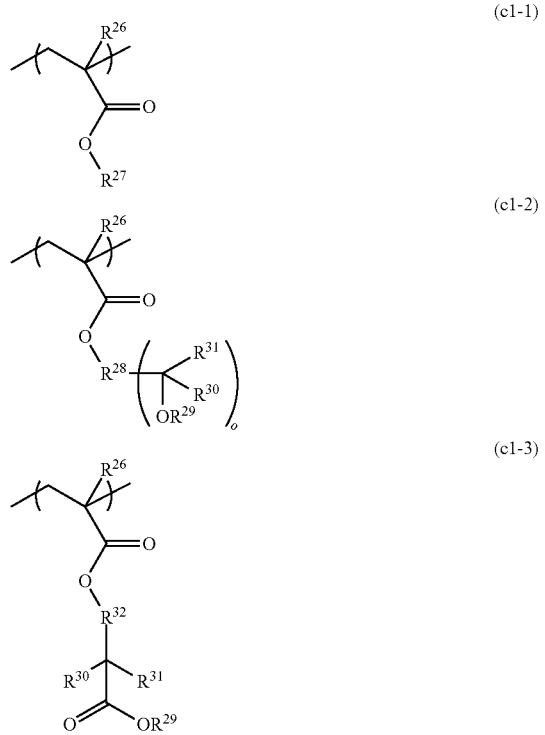

In the above formulae (c1-1) to (c1-3), $R^{26}$ each independently represents a hydrogen atom, a lower alkyl group or a halogenated lower alkyl group; $R^{27}$ represents a fluorinated alkyl group having 1 to 30 carbon atoms or a fluorinated alicyclic hydrocarbon group having 3 to 30 carbon atoms; $R^{28}$ represents a linking group having a valency of (o+1); $R^{29}$ represents a hydrogen atom, a monovalent organic group that includes an acid-dissociable group or a base-dissociable group; o is an integer of 1 to 3; $R^{30}$ and $R^{31}$ each independently represent a hydrogen atom, a fluorine atom or a fluorinated alkyl group having 1 to 30 carbon atoms, wherein provided that $R^{29}$, $R^{30}$ and $R^{31}$ are each present in a plurality of number, the plurality of $R^{29}$s, $R^{30}$s and $R^{31}$s may be the same or different, but any case where all the $R^{30}$ and $R^{31}$ represent a hydrogen atom is excluded; and $R^{32}$ represents a bivalent linking group.

The fluorinated alkyl group having 1 to 30 carbon atoms represented by the $R^{27}$ is exemplified by a linear or branched alkyl group having 1 to 6 carbon atoms and being substituted with at least one or more fluorine atoms(s) or a group derived therefrom, or the like. The fluorinated alicyclic hydrocarbon group having 3 to 30 carbon atoms represented by the $R^{27}$ is exemplified by a monovalent alicyclic hydrocarbon group having 4 to 20 carbon atoms and being substituted with at least 1 one or more fluorine atom(s) or or a group derived therefrom, or the like.

Examples of the linear or branched alkyl group having 1 to 6 carbon atoms include a methyl group, an ethyl group, a propyl group, a butyl group, a pentyl group, a hexyl group, and the like.

Examples of the monovalent alicyclic hydrocarbon group having 4 to 20 carbon atoms or a group derived therefrom include a cyclopentyl group, a cyclopentylmethyl group, a 1-(1-cyclopentylethyl) group, a 1-(2-cyclopentylethyl) group, a cyclohexyl group, a cyclohexylmethyl group, a 1-(1-cyclohexylethyl) group, a 1-(2-cyclohexylethyl) group, a cycloheptyl group, a cycloheptylmethyl group, a 1-(1-cycloheptylethyl) group, a 1-(2-cycloheptylethyl) group, and the like.

Examples of the monomer that gives the structural unit (c1-1) include trifluoromethyl(meth)acrylic acid ester, 2,2,2-trifluoroethyl(meth)acrylic acid ester, perfluoroethyl (meth)acrylic acid ester, perfluoro n-propyl(meth)acrylic acid ester, perfluoro i-propyl(meth)acrylic acid ester, perfluoro n-butyl (meth)acrylic acid ester, perfluoro i-butyl (meth)acrylic acid ester, perfluoro t-butyl(meth)acrylic acid ester, 2-(1,1,1,3,3,3-hexafluoropropyl)(meth)acrylic acid ester, 1-(2,2,3,3,4,4,5,5-octafluoropentyl)(meth)acrylic acid ester, perfluorocyclohexylmethyl(meth)acrylic acid ester, 1-(2,2,3,3,3-pentafluoropropyl)(meth)acrylic acid ester, 1-(3,3,4,4,5,5,6,6,7,7,8,8,9,9,10,10,10-heptadecafluorodecyl) (meth)acrylic acid ester, 1-(5-trifluoromethyl-3,3,4,4,5,6,6,6-octafluorohexyl)(meth)acrylic acid ester, and the like. Of these, trifluoromethyl(meth)acrylic acid ester, and 2,2,2-trifluoroethyl (meth)acrylic acid ester are preferred.

In the above formulae (c1-2) and (c1-3), a partial structure represented by the following formula is exemplified by groups represented by the following formulae (f1) to (f5), and the like.

-continued

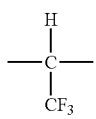 (f2)

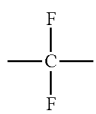 (f3)

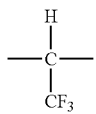 (f4)

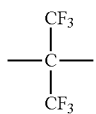 (f5)

Of these, the group represented by the above formula (f5) is preferred in the formula (c1-2). The group represented by the above formula (f3) is preferred in the formula (c1-3).

Examples of the monomer that gives the structural unit (c1-2) include compounds represented by the following formulae, and the like.

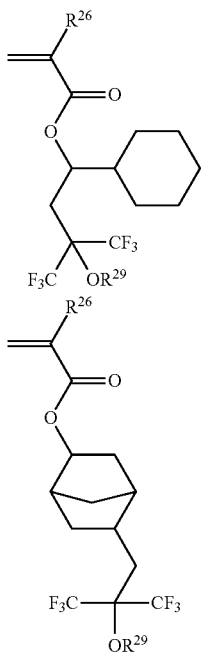
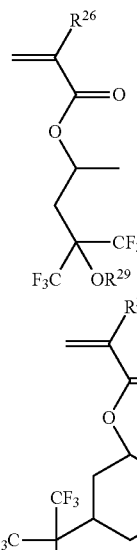
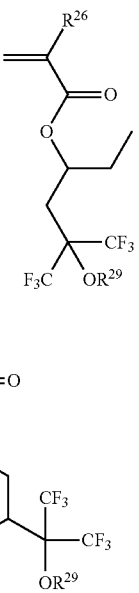

In the above formulae, $R^{26}$ and $R^{29}$ are as defined in the above formula (c1-2).

Examples of the monomer that gives the structural unit (c1-3) include compounds represented by the following formulae, and the like.

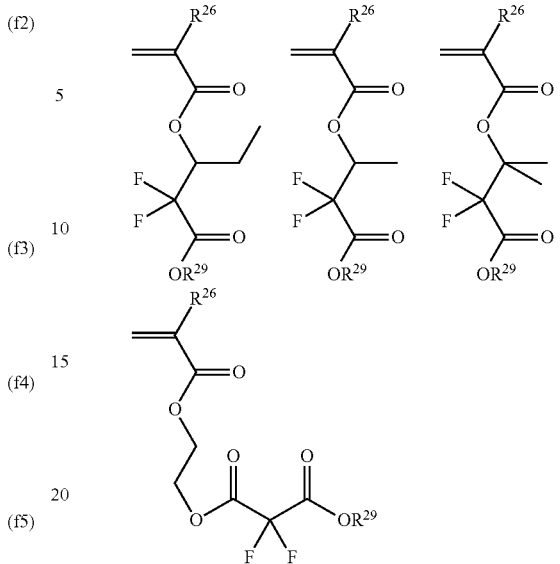

In the above formula, $R^{26}$ and $R^{29}$ are as defined in the above formula (c1-3).

[Structural Unit (c2)]

Examples of the structural unit (c2) include a structural unit represented by the following formula (5), and the like.

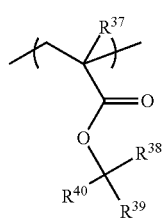

(5)

In the above formula (5), $R^{37}$ represents a hydrogen atom, a methyl group, a trifluoromethyl group or a hydroxymethyl group; $R^{38}$, $R^{39}$ and $R^{40}$ each independently represent linear or branched alkyl group having 1 to 4 carbon atoms, or an alicyclic hydrocarbon group having 4 to 20 carbon atoms or a group derived therefrom; wherein $R^{39}$ and $R^{40}$ may taken together represent a bivalent alicyclic hydrocarbon group having 4 to 20 carbon atoms or a group derived therefrom by binding with each other together with the carbon atom to which they bond.

The structural unit (c2) is preferably a structural unit represented by the following formula (5-1).

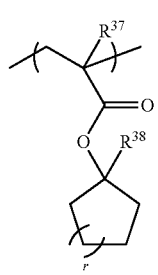

(5-1)

In the above formula (5-1), $R^{37}$ is as defined in the above formula (5); $R^{38}$ represents a linear or branched alkyl group having 1 to 4 carbon atoms; and r is an integer of 1 to 4.

Examples of the monomer that gives the structural unit (c2) include (meth)acrylic acid 1-methyl-1-cyclopentyl ester, (meth)acrylic acid 1-ethyl-1-cyclopentyl ester, (meth)acrylic acid 1-isopropyl-1-cyclopentyl ester, (meth)acrylic acid 1-methyl-1-cyclohexyl ester, (meth)acrylic acid 1-ethyl-1-cyclohexyl ester, (meth)acrylic acid 1-ethyl-1-cyclooctyl ester, and the like. Of these, (meth)acrylic acid 1-methyl-1-cyclopentyl ester and (meth)acrylic acid 1-ethyl-1-cyclooctyl ester are preferred.

The proportion of the structural unit (c1) contained is preferably 20 mol % to 90 mol %, and more preferably 20 mol % to 80 mol % with respect to the total of the structural units constituting the fluorine atom-containing polymer (C). When the proportion of the structural unit (c1) falls within the above specific range, elution of the acid generating agent, an acid diffusion control agent and the like in the resist film into a liquid for immersion lithography can be further inhibited. In addition, due to an additional increase in a receding contact angle between the resist film and the liquid for immersion lithography, water droplets derived from the liquid for immersion lithography are less likely to remain on the resist film, thereby enabling defects caused by the liquid for immersion lithography to be more efficiently suppressed.

The proportion of the structural unit (c2) contained is preferably no greater than 80 mol %, and more preferably 20 mol % to 80 mol % with respect to the total of the structural units constituting the fluorine atom-containing polymer (C). The content of the structural unit (c2) falling within the above specific range is favorable in that the difference between an advancing contact angle and a receding contact angle can be decreased, and thus follow ability of a liquid immersion liquid is improved in liquid immersion lithography, thereby enabling a response to high-speed scanning.

<Synthesis Method of (C) Fluorine Atom-Containing Polymer>

As a method for synthesizing the fluorine atom-containing polymer (C), a method of producing the base polymer (B) can be suitably applied.

The Mw of the fluorine atom-containing polymer (C) is preferably 1,000 to 50,000, more preferably 1,000 to 40,000 and particularly preferably 1,000 to 30,000 in terms of the polystyrene equivalent according to a GPC method. When the Mw is less than 1,000, a resist film having a sufficient receding contact angle may not be obtained. To the contrary, when the Mw exceeds 50,000, developability of the resist film may be decreased. The Mw/Mn is preferably 1 to 5 and more preferably 1 to 4.

The fluorine atom content of the fluorine atom-containing polymer (C) is preferably greater than that of the base polymer (B). The fluorine atom content of the fluorine atom-containing polymer (C) is typically no less than 5% by mass, preferably 5% by mass to 50% by mass, and more preferably 5% by mass to 40% by mass.

<(D) Acid Diffusion Control Agent>

The radiation-sensitive resin composition may contain the acid diffusion control agent (D) as a suitable component. When the radiation-sensitive resin composition contains the acid diffusion control agent (D), resist pattern configuration and dimension fidelity can be improved.

The acid diffusion control agent (D) is exemplified by a compound represented by the following formula (6) (hereinafter, may be also referred to as "nitrogen-containing compound (I)"), a compound having three or more nitrogen atoms (hereinafter, may be also referred to as "nitrogen-containing compound (III)"), a nitrogen-containing heterocyclic compound, and the like.

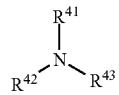

(6)

In the above formula (6), $R^{41}$, $R^{42}$ and $R^{43}$ each independently represent a hydrogen atom, a linear, branched or cyclic alkyl group, aryl group or aralkyl group which are unsubstituted or optionally substituted, or an acid-dissociable group.

The nitrogen-containing compound (II) is exemplified by N,N,N',N'-tetrakis(2-hydroxypropyl)ethylene diamine, and the like. The nitrogen-containing compound (III) is exemplified by polymers such as polyethyleneimine, polyallylamine and dimethylaminoethylacrylamide, and the like. The nitrogen-containing heterocyclic compound is exemplified by 2-phenylbenzimidazole, N-t-butoxycarbonyl-2-phenylbenzimidazole, and the like.

In addition, a compound represented by the following formula (7) may be also used as the acid diffusion control agent (D).

(7)

In the above formula (7), $Y^+$ represents a cation represented by the following formula (7-1) or (7-2); $Z^-$ represents $OH^-$, $R^{49}$—$COO^-$, or $R^{49}$—$SO_3^-$; and $R^{49}$ represents an unsubstituted or optionally substituted alkyl group, alicyclic hydrocarbon group or aryl group.

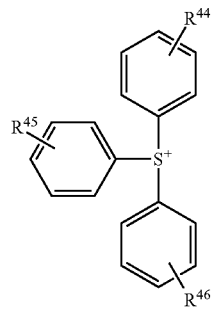

(7-1)

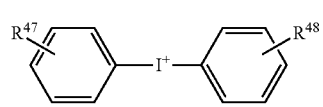

(7-2)

In the above formula (7-1), $R^{44}$, $R^{45}$ and $R^{46}$ each independently represent a hydrogen atom, an alkyl group, an alkoxy group, a hydroxyl group or a halogen atom. In the above formula (7-2), $R^{47}$ and $R^{48}$ each independently represent a hydrogen atom, an alkyl group, an alkoxy group, a hydroxyl group or a halogen atom.

The compound is used as the acid diffusion control agent (D) that is degraded by exposure and lose acid diffusion controllability, i.e., a photodegradable acid diffusion control agent as generally referred to. Due to including the photodegradable acid diffusion control agent, an acid is diffused at sites exposed with light whereas diffusion of an acid is controlled at sites not exposed with light, thereby resulting in excellent contrast between the site exposed with light and the site not exposed with light; therefore, in particular, LWR and MEEF of the radiation-sensitive resin composition can be effectively improved.

The content of the acid diffusion control agent (D) is preferably no greater than 10 parts by mass, and more preferably no greater than 5 parts by mass with respect to 100 parts by mass of the base polymer (B). When the content of the acid diffusion control agent (D) exceeds 10 parts by mass, sensitivity of the resist film formed tends to be decreased.

<Other Optional Components>

The radiation-sensitive resin composition may include in addition to the specified acid generating agent (A1), the base polymer (B), the fluorine atom-containing polymer (C) and the acid diffusion control agent (D), other optional components such as a surfactant within the range not to impair the effects of the present invention.

[Surfactant]

A surfactant is a component that exhibits an effect of improving a coating property, developability, and the like. Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate, and the like. Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate, and the like. Examples of commercially available products include KP341 (manufactured by Shin-Etsu Chemical Co., Ltd.), Polyflow No. 75 and Polyflow No. 95 (both manufactured by Kyoeisha Chemical Co., Ltd.), EFTOP EF301, EFTOP EF303 and EFTOP EF352 (all manufactured by TOCHEM PRODUCTS CO. LTD.), MEGAFAC F171 and MEGAFAC F173 (both manufactured by Dainippon Ink And Chemicals, Incorporated), Fluorad™ FC430 and Fluorad™ FC431 (both manufactured by Sumitomo 3M Ltd., AashiGuard AG710, Surflon S-382, Surflon SC-101, Surflon SC-102, Surflon SC-103, Surflon SC-104, Surflon SC-105 and Surflon SC-106 (all manufactured by Asahi Glass Co., Ltd.), and the like. The content of the surfactant is typically no greater than 2 parts by mass with respect to 100 parts by mass of the base polymer (B).

<Preparation Method of Radiation-Sensitive Resin Composition>

The radiation-sensitive resin composition is usually prepared to form a composition solution by dissolving in a solvent so as to give the total solid content of 1% by mass to 50% by mass and preferably 3% by mass to 25% by mass, followed by filtration through a filter having a pore size of, for example, about 0.1 μm.

The solvent used in preparing the radiation-sensitive resin composition is exemplified by an alcohol solvent, a ketone solvent, an amide solvent, an ether solvent, an ester solvent and a mixed solvent, and the like.

Examples of the alcohol solvent include monoalcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethyl nonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

partially etherified polyhydric alcohol solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether, and the like.

Examples of the ketone solvent include chain ketone solvents such as acetone, methyl ethyl ketone, methyl-n-propyl ketone, methyl-n-butyl ketone, diethyl ketone, methyl-iso-butyl ketone, methyl-n-pentyl ketone, ethyl-n-butyl ketone, methyl-n-hexyl ketone, di-iso-butyl ketone and trimethyl nonanone;

cyclic ketone solvents such as cyclopentanone, cyclohexanone, cycloheptanone, cyclooctanone and methylcyclohexanone;

2,4-pentanedione, acetonyl acetone, diacetone alcohol, acetophenone, and the like.

Examples of the amide solvent include cyclic amide solvents such as N,N'-dimethylimidazolidinone and N-methylpyrrolidone;

chain amide solvents such as N-methylformamide, N,N-dimethylformamide, N,N-diethylformamide, acetamide, N-methylacetamide, N,N-dimethylacetamide and N-methylpropionamide.

Examples of the ester solvent include carbonic acid esters such as diethyl carbonate and propylene carbonate;

lactone solvents such as γ-butyrolactone and γ-valerolactone;

acetic acid esters such as methyl acetate, ethyl acetate, n-propyl acetate, iso-propyl acetate, n-butyl acetate, iso-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate and n-nonyl acetate;

acetoacetic acid ester solvents such as methyl acetoacetate and ethyl acetoacetate;

polyhydric alcohol monoalkyl ether acetate solvents such as ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate and dipropylene glycol monoethyl ether acetate;

diglycol acetate, methoxytriglycol acetate, ethyl propionate, n-butyl propionate, iso-amyl propionate, diethyl oxalate, di-n-butyl oxalate, methyl lactate, ethyl lactate, n-butyl lactate, n-amyl lactate, diethyl malonate, dimethyl phthalate and diethyl phthalate, and the like.

Examples of the other solvent include aliphatic hydrocarbon solvents such as n-pentane, iso-pentane, n-hexane, iso-hexane, n-heptane, iso-heptane, 2,2,4-trimethyl pentane, n-octane, iso-octane, cyclohexane and methylcyclohexane;

aromatic hydrocarbon solvents such as benzene, toluene, xylene, mesitylene, ethylbenzene, trimethyl benzene, methylethylbenzene, n-propylbenzene, iso-propylbenzene, diethyl benzene, iso-butylbenzene, triethyl benzene, di-iso-propylbenzene and n-amyl naphthalene;

halogen-containing solvents such as dichloromethane, chloroform, chlorofluorocarbon, chlorobenzene and dichlorobenzene, and the like.

Among these solvents, an ester solvent and a ketone solvent are preferred, a polyhydric alcohol monoalkyl ether acetate solvent, a cyclic ketone solvent and a lactone solvent are more preferred, and propylene glycol monomethyl ether acetate, cyclohexanone and y-butyrolactone are preferred. These solvents may be used alone, or in combination of two or more thereof.

<Formation Method of a Resist Pattern>

The method for forming a resist pattern of the embodiment of the present invention includes:

(1) a step of forming a resist film on a substrate using the radiation-sensitive resin composition;

(2) a step of exposing the formed resist film; and (3) a step of developing the exposed resist film.

According to the formation method, a resist pattern having favorable LWR can be formed since the radiation-sensitive resin composition described above is used.

In addition, the exposure in the step (2) is preferably liquid immersion lithography. Since the formation method can adopt even a liquid immersion lithography step, a finer resist pattern can be formed, and is thus suitable for a lithography process by which microfabrication is expected to further advance in the future.

In the step (1), a resist film is formed by coating a solution of the radiation-sensitive resin composition on a substrate such as, for example, a silicon wafer, or a wafer coated with aluminum by an appropriate coating means such as means of spin coating, cast coating or roll coating. Specifically, after a solution of the radiation-sensitive resin composition is coated such that the resist film has a predetermined film thickness, prebaking (PB) is carried out to allow the solvent in the coating film to be volatilized, whereby a resist film is formed.

The film thickness of the resist film is preferably 10 nm to 1,000 nm, and more preferably 20 nm to 300 nm.

The temperature of PB may depend on the formulation of the radiation-sensitive resin composition, and is preferably 30° C. to 200° C. and more preferably 50° C. to 150° C. The time period of PB is about 30 sec to 600 sec.

In the step (2), the resist film formed in the step (1) is exposed by irradiating with a radioactive ray. Conditions of the exposure such as the exposure dose may be appropriately selected in accordance with the formulation of the radiation-sensitive resin composition, and the type of the additives, etc. The radioactive ray employed is appropriately selected from visible light rays, ultraviolet rays, far ultraviolet rays, X-rays, charged particle rays and the like in accordance with the type of the acid generating agent used. The radioactive ray is preferably a far ultraviolet ray, more preferably an ArF excimer laser beam (wavelength: 193 nm) and a KrF excimer laser beam (wavelength: 248 nm), and still more preferably an ArF excimer laser.

When liquid immersion lithography is employed, a liquid for immersion lithography is provided, and a radioactive ray is irradiated through the liquid for immersion lithography.

The liquid for immersion lithography is exemplified by pure water, a long chain or cyclic aliphatic compound, and the like.

Post exposure baling (PEB) is preferably carried out after the exposure. The PEB enables a dissociation reaction of the acid-dissociable group in the polymer component to smoothly proceed. The temperature of the PEB may depend on the formulation of the radiation-sensitive resin composition, and is typically 30° C. to 200° C., and preferably 50° C. to 170° C. The time period of PEB is about 30 sec to 60 sec.

In the embodiment of present invention, in order to maximize the potential capability of the radiation-sensitive resin composition, an organic or inorganic antireflection film may be also formed on the substrate employed, as disclosed in, for example, Japanese Examined Patent, Publication No. H6-12452 (Japanese Unexamined Patent Application, Publication No. S59-93448), and the like. Moreover, in order to prevent influences of basic impurities etc., included in the environment atmosphere, a protective film may be also provided on the resist film, as disclosed in, for example, Japanese Unexamined Patent Application, Publication No. H5-188598, and the like. Furthermore, in order to prevent effluence of the acid generating agent etc., from the resist film during the liquid immersion lithography, a protective film for liquid immersion may be provided on the resist film, as disclosed in, for example, Japanese Unexamined Patent Application, Publication No. 2005-352384, and the like. Additionally, these techniques may be used in combination.

In the step (3), the resist film exposed in the step (2) is developed. Examples of preferable developer solution used in the development step include aqueous alkali solutions prepared by dissolving at least one alkaline compound such as sodium hydroxide, potassium hydroxide, sodium carbonate, sodium silicate, sodium metasilicate, ammonia water, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo[5.4.0]-7-undecene or 1,5-diazabicyclo[4.3.0]-5-nonene.

The concentration of the alkaline aqueous solution is preferably no greater than 10% by mass. In the case in which the concentration of the alkaline aqueous solution is greater than 10% by mass, sites unexposed with light may be also dissolved in the developing solution. In addition, an organic solvent may be also added to the developing solution consisting of the aforementioned alkaline aqueous solution.

It is to be noted that the development with a developer solution consisting of the alkaline aqueous solution is, in general, followed by washing with water and drying. Furthermore, in the step (3), a developer solution containing an organic solvent as a principal component may be also used. In this case, the development is followed by washing with an organic solvent and drying, in general.

<Acid Generating Agent and Compound>

An embodiment of the present invention involves an acid generating agent that generates by irradiation with a radioactive ray the compound represented by the above formula (1). Since the acid generating agent is a monofluorosulfonic acid type acid generating agent, an acid having lower acidity is generated upon exposure as compared with conventional difluorosulfonic acid type acid generating agents; therefore, radiation-sensitive resin composition containing the acid generating agent can form a resist pattern having satisfactory LWR.

In addition, further embodiment of the present invention involves the compound represented by the above formula (1).

The compound is suitable as a basic material for producing the acid generating agent of the embodiment of the present invention, and the like.

With respect to details, preferable embodiments and the like of the acid generating agent and the compound, the context set forth in the section of the specified acid generating agent (A1) contained in the radiation-sensitive resin composition is applicable; therefore, explanation of the same is omitted herein.

Hereinafter, the present invention will be explained more specifically by way of Examples, but the present invention is not limited to these Examples.

<Synthesis of (A1) Specified Acid Generating Agent>

Synthesis Example 1

Into a 300 mL three-neck flask purged with nitrogen were added 4.32 g (16.4 mmol) of 1,4,7,10,13,16-hexaoxacyclooctadecane (18-crown-6), 16.2 g (0.28 mol) of potassium fluoride (spray dried product) and 60 mL of dehydrated toluene to prepare a suspension liquid. Thereto was slowly added dropwise 23.6 g (92 mmol) of 1-adamantyl bromomethyl ketone dissolved in 50 mL of toluene. The temperature of the reaction solution was elevated to 80° C., and heated for 6 hrs. The reaction solution was cooled to a normal temperature, and 150 mL of ultra pure water was added, followed by an operation of liquid separation to recover an organic layer. This organic layer was washed three times with ultra pure water, and the solvent was vacuum distilled to obtain 15.6 g of a compound (a-1) represented by the following formula (1-adamantyl fluoromethyl ketone) (yield: 86%, purity: 99.5%).

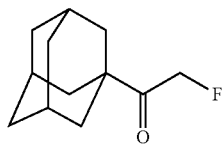

(a-1)

Synthesis Example 2

Into a 300 mL three-neck flask purged with nitrogen were added 8.81 g (44.9 mmol) of the compound (a-1) and 100 mL of tetrahydrofuran to permit dissolution, and a solution prepared by dissolving 28.71 g (90 mmol) of pyridinium bromide perbromide in 50 mL of tetrahydrofuran was slowly added thereto. Thereafter, the mixture was stirred at a normal temperature for 3 hrs. After completing the reaction, 100 mL of dichloromethane and 100 mL of ultra pure water were added, followed by an operation of liquid separation to recover an organic layer. The organic layer was concentrated by vacuum distillation. The concentrated liquid was purified by column chromatography to obtain 10.9 g of a compound (a-2) represented by the following formula (1-adamantyl bromofluoromethyl ketone) (yield: 88.3%, purity: 95.0%).

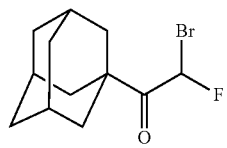

(a-2)

Synthesis Example 3

Into a 200 mL recovery flask purged with nitrogen were added 8.25 g (0.03 mol) of the compound (a-2), 100 mL of dehydrated toluene, 9.31 g (0.15 mol) of ethylene glycol and 0.25 g (1.5 mmol) of p-toluenesulfonic acid. A Dean and Stark tube was attached to the flask, and the mixture was refluxed while heating for 6 hrs. An aqueous saturated sodium bicarbonate solution was added to the reaction liquid, followed by an operation of liquid separation to recover an organic layer. The organic layer was washed with an aqueous saturated sodium bicarbonate solution, and the solvent was vacuum distillated to obtain 7.0 g of a compound (a-3) represented by the following formula (yield: 73%, purity: 88%).

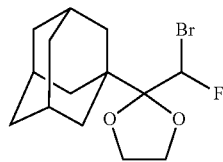

(a-3)

Example 1

Into a 300 mL three-neck flask purged with nitrogen were charged 6.8 g (0.04 mol) of sodium hydrosulfite and 3.36 g (0.04 mol) of sodium bicarbonate, which were dissolved in 50 mL of ultra pure water. Thereto was slowly added dropwise 50 mL of a solution of 6.52 g (0.02 mol) of the compound (a-3) in acetonitrile. Thereafter, the temperature of the reaction liquid was elevated, and the liquid was refluxed while heating for 6 hrs. After completing the reaction, the reaction liquid was cooled to normal temperature, to which 0.33 g (1 mmol) of disodium tungstate was added, and 6.6 g (0.06 mol) of a 31% by mass aqueous hydrogen peroxide solution was slowly added dropwise. After stirring the mixture at normal temperature for 2 hrs, sodium sulfite was added to quench excess hydrogen peroxide. Diluted hydrochloric acid was added to the reaction liquid to adjust the pH to 3, and the mixture was stirred for 1 hour. Thereafter, a solution prepared by dissolving 5.98 g (0.02 mol) of triphenylsulfonium chloride in 50 mL of ultra pure water was added to the reaction liquid, followed by stirring for 1 hour. Thereafter, the reaction liquid was extracted with dichloromethane, and the organic layer was washed with ultra pure water five times, followed by vacuum distillation of the solvent to obtain 8.1 g of a compound represented by the following formula (A1-1). The structure of the compound (A1-1) was confirmed by a $^1$H-NMR analysis. It is to be noted that a nuclear magnetic resonance apparatus (manufactured by JEOL, Ltd., JNM-ECP500) was used for the $^1$H-NMR analysis.

$^1$H-NMR (solvent used in determination: CDCl$_3$, standard substance: tetramethylsilane) δ: 7.81 (m, 6H), 7.65-7.76 (m, 9H), 5.70 (d, 1H), 1.92 (s, 3H), 1.63-1.75 (m, 12H)

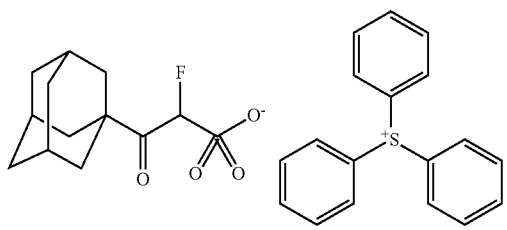

(A1-1)

Example 2

Into a 300 ml three-neck flask purged with nitrogen were charged 6.8 g (0.04 mol) of sodium hydrosulfite and 3.36 g (0.04 mol) of sodium bicarbonate, which were dissolved in 50 mL of ultra pure water. Thereto was slowly added dropwise 50 mL of a solution of 4.93 g (0.02 mol) of 1-adamantyl chlorofluoroacetate in acetonitrile. Thereafter, the temperature of the reaction liquid was elevated, and the liquid was refluxed while heating for 13 hrs. After completing the reaction, the reaction liquid was cooled to normal temperature, to which 0.33 g (1 mmol) of disodium tungstate was added, and 6.6 g (0.06 mol) of a 31% by mass aqueous hydrogen peroxide solution was slowly added dropwise. After stirring the mixture at normal temperature for 2 hrs, sodium sulfite was added to quench excess hydrogen peroxide. Diluted hydrochloric acid was added to the reaction liquid to adjust the pH to 3, and the mixture was stirred for 1 hour. Thereafter, a solution prepared by dissolving 5.98 g (0.02 mol) of triphenylsulfonium chloride in 50 mL of ultra pure water was added to the reaction liquid, followed by stirring for 1 hour. Thereafter, the reaction liquid was extracted with dichloromethane, and the organic layer was washed with ultra pure water five times, followed by vacuum distillation of the solvent to obtain 8.8 g of a compound represented by the following formula (A1-2). The structure of the compound (A1-2) was confirmed by a $^1$H-NMR analysis using the aforementioned nuclear magnetic resonance apparatus.

$^1$H-NMR (solvent used in determination: CDCl$_3$, standard substance: tetramethylsilane) δ: 7.81 (m, 6H), 7.65-7.76 (m, 9H), 5.80 (d, 1H), 1.92 (s, 3H), 1.63-1.75 (m, 12H)

(A1-2)

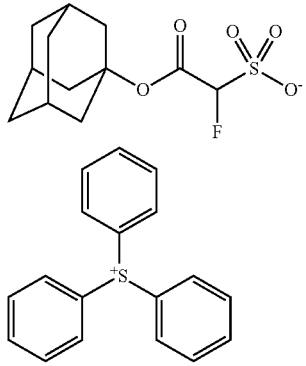

<Synthesis of (B) Base Polymer>

Synthesis Example 4

A monomer solution was prepared by dissolving 11.92 g a compound (M-1) represented by the following formula, 41.07 g of the compound (M-2), 15.75 g of the compound (M-3), 11.16 g of the compound (M-4) and 20.10 g of the compound (M-5) and 3.88 g of dimethyl 2,2'-azobis(2-isobutyronitrile) in 200 g of 2-butanone. Into a 1,000 mL three-neck flask was charged 100 g of 2-butanone, and nitrogen was purged for 30 min, followed by heating the reaction vessel at 80° C. while stirring the mixture. Thereto was added the monomer solution as described above dropwise over 4 hrs, and after completing the dropwise addition, the solution was aged at 80° C. for 2 hrs. After completing the polymerization, the polymerization solution was water cooled to lower the temperature to no greater than 30° C. The polymerization solution was vacuum concentrated with an evaporator until the mass of the polymerization solution became 200 g. Thereafter, the polymerization liquid was charged into 1,000 g of methanol to execute a reprecipitation operation. The precipitated slurry was filtered by vacuum filtration, and the solid content was washed with methanol three times. The obtained powder was vacuum dried at 60° C. for hrs to obtain 88.0 g (yield: 88%) of a white powder (polymer (B-1)). The polymer (B-1) had a Mw of 9,300, and the Mw/Mn of 1.60. As a result of the $^{13}$C-NMR analysis, proportions of structural units derived from the compounds (M-1), (M-2), (M-3), (M-4) and (M-5) were 16 mol % (structural unit (b1)), 26 mol % (structural unit (b1)), 19 mol % (structural unit (b2)), 11 mol % (other structural unit) and 28 mol % (structural unit (b2)), respectively. It is to be noted that (JNM-ECP500 manufactured by JEOL, Ltd.) was used for the $^{13}$C-NMR analysis. The fluorine atom content was 0% by mass.

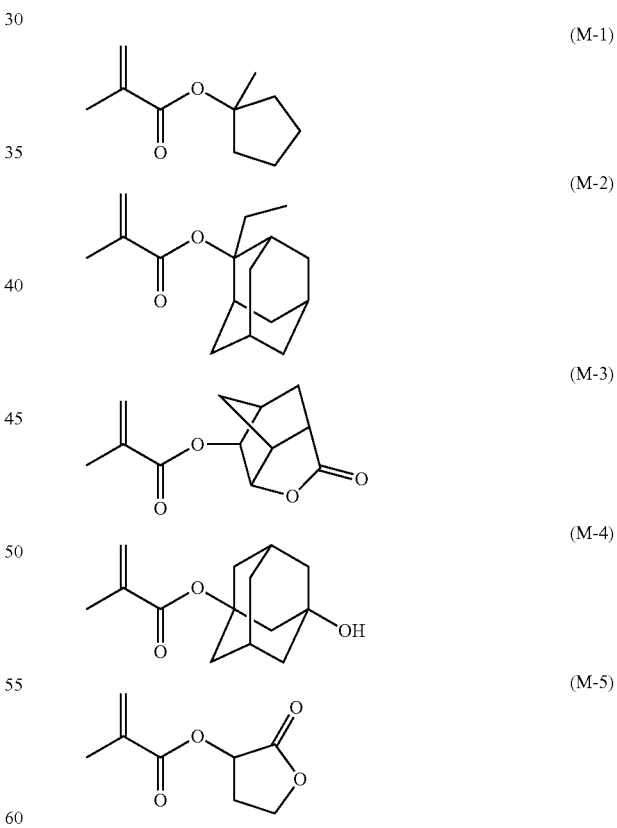

<Synthesis of (C) Fluorine Atom-Containing Polymer>

Synthesis Example 5

A compound (M-6) represented by the following formula in an amount of 3.8 g and 1.2 g of the compound (M-7) were dissolved in 10 g of 2-butanone, and further 0.09 g of 2,2'-azobis(2-isobutyronitrile) was charged in a 100 mL three-neck flask. After nitrogen was purged for 30 min, the reaction vessel was heated to 80° C. while stirring the mixture. The polymerization reaction was carried out for 6 hrs from the time when heating was started which was assumed to be a start time point of polymerization. After completing the polymerization, the polymerization solution was water cooled to lower the temperature to no greater than 30° C. and vacuum concentrated with an evaporator until the mass of the polymerization solution became 12.5 g. The polymerization liquid was slowly charged into 75 g of n-hexane which had been cooled to 0° C. to allow the solid content to be precipitated. The mixed liquid was filtered, and the solid content was washed with n-hexane. The powder thus obtained was vacuum dried at 40° C. for 15 hrs to obtain 3.75 g of a white powder (polymer (C-1)) (yield: 75%). The polymer (C-1) had an Mw of 9,400, and the Mw/Mn of 1.50. As a result of the $^{13}$C-NMR analysis, proportions of structural units derived from the compounds (M-6) and (M-7) were 68.5 mol % (structural unit (c1)) and 31.5 mol % (structural unit (c2)), respectively. The fluorine atom content was 21.4% by mass.

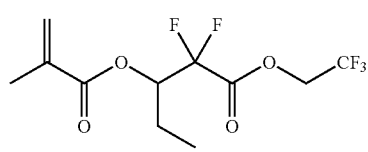
(M-6)

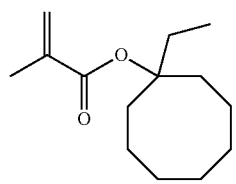
(M-7)

Synthesis Example 6

A compound (M-8) represented by the following formula in an amount of 4.06 g and 0.94 g of the compound (M-7) represented by the above formula were dissolved in 10 g of 2-butanone, and further 0.07 g of 2,2'-azobis(2-isobutyronitrile) was charged in a 100 mL three-neck flask. After nitrogen was purged for 30 min, the reaction vessel was heated to 80° C. while stirring the mixture. The polymerization reaction was carried out for 6 hrs from the time when heating was started which was assumed to be a start time point of polymerization. After completing the polymerization, the polymerization solution was water cooled to lower the temperature to no greater than 30° C. and vacuum concentrated with an evaporator until the mass of the polymerization solution became 12.5 g. The polymerization liquid was slowly charged into 75 g of n-hexane which had been cooled to 0° C. to allow the solid content to be precipitated. The mixed liquid was filtered, and the solid content was washed with n-hexane. The powder thus obtained was vacuum dried at 40° C. for 15 hrs to obtain 3.5 g of a white powder (polymer (C-2)) (yield: 70%). The polymer (C-2) had an Mw of 11,400, and the Mw/Mn of 1.50. As a result of the $^{13}$C-NMR analysis, proportions of structural units derived from the compounds (M-8) and (M-7) were 70.9 mol % (structural unit (c1)) and 29.1 mol % (structural unit (c2)), respectively. The fluorine atom content was 19.4% by mass.

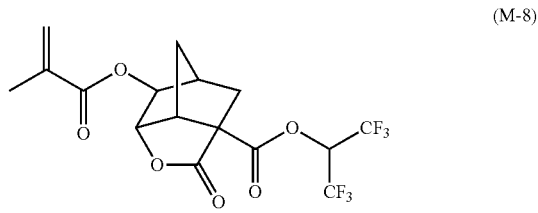
(M-8)

Synthesis Example 7

A compound (M-9) represented by the following formula in an amount of 1.42 g and 3.58 g of the compound (M-10) were dissolved in 10 g of 2-butanone, and further 0.14 g of 2,2'-azobis(2-isobutyronitrile) was charged in a 100 mL three-neck flask. After nitrogen was purged for 30 min, the reaction vessel was heated to 80° C. while stirring the mixture. The polymerization reaction was carried out for 6 hrs from the time when heating was started which was assumed to be a start time point of polymerization. After completing the polymerization, the polymerization solution was water cooled to lower the temperature to no greater than 30° C. and vacuum concentrated with an evaporator until the mass of the polymerization solution became 12.5 g. The polymerization liquid was slowly charged into 75 g of n-hexane which had been cooled to 0° C. to allow the solid content to be precipitated. The mixed liquid was filtered, and the solid content was washed with n-hexane. The powder thus obtained was vacuum dried at 40° C. for 15 hrs to obtain 3.85 g of a white powder (polymer (C-3)) (yield: 77%). The polymer (C-3) had an Mw of 7,400, and the Mw/Mn of 1.50. As a result of the $^{13}$C-NMR analysis, proportions of structural units derived from the compounds (M-9) and (M-10) were 30.5 mol % (structural unit (c1)) and 69.5 mol % (structural unit (c2)), respectively. The fluorine atom content was 10.3% by mass.

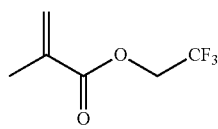
(M-9)

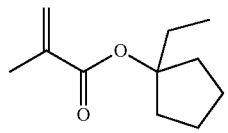
(M-10)

<Preparation of Radiation-Sensitive Resin Composition>

Details of each component used in Examples and Comparative Examples are shown below.

(A2) Acid generating agent

A2-1: a compound represented by the following formula (A2-1)

A2-2: a compound represented by the following formula (A2-2)

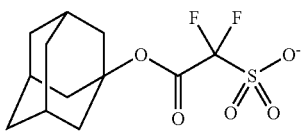
(A2-1)

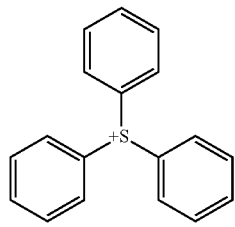

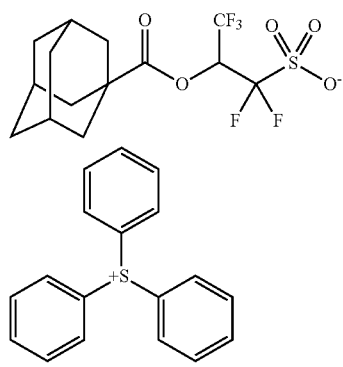
(A2-2)

(D) Acid Diffusion Control Agent
D-1: a compound represented by the following formula (D-1)
D-2: a compound represented by the following formula (D-2)
D-3: a compound represented by the following formula (D-3)

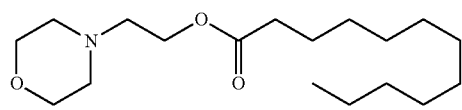
(D-1)

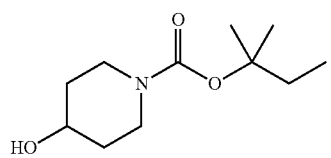
(D-2)

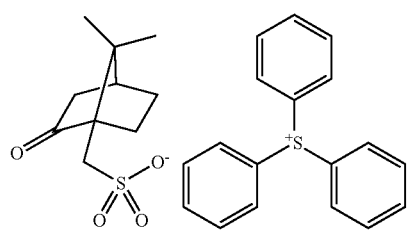
(D-3)

(E) Solvent
E-1: propylene glycol monomethyl ether acetate
E-2: cyclohexanone
E-3: γ-butyrolactone Example 3

A solution was provided by adding 8 parts by mass of the compound (A-1) as the specified acid generating agent (A1), 100 parts by mass of (B-1) as the base polymer (B), 5 parts by mass of (C-1) as the fluorine atom-containing polymer (C), and 0.6 parts by mass of (D-1) as the acid diffusion control agent (D) to a mixture of 1,881 parts by mass of (E-1), 806 parts by mass of (E-2) and 200 parts by mass of (E-3) as the solvent (E). This solution was filtered through a membrane filter having a pore size of 0.1 μm to prepare a radiation-sensitive resin composition.

Examples 4 to 12 and Comparative Examples 1 to 3

Each radiation-sensitive resin composition was prepared by a similar operation to Example 3 except that each component of the type and in the amount shown in Table 1 was used.

<Evaluation>

Using each radiation-sensitive resin composition, the following characteristics were evaluated. The evaluation results are shown in Table 1 all together.

[LWR]

ARC66 (manufactured by Nissan Chemical Industries, Ltd.) was applied on the surface of a silicon wafer having a diameter of 12 inch by spin coating. Next, the wafer was baked at 205° C. for 60 sec to form an underlayer film having a film thickness of 105 nm. Each prepared radiation-sensitive resin composition was spin-coated on the substrate having the underlayer film thus formed, and prebaked at 100° C. for 50 sec, followed by cooling at 23° C. for 30 sec to form a resist film having a film thickness of 90 nm. Subsequently, the substrate was exposed using ArF Immersion Scanner (S610C, manufactured by NIKON) through a mask for projecting a bright field pattern having a line of 40 nm and a pitch of 80 nm, under an optical condition involving NA of 1.30, a ratio of outer σ/inner σ being 0.977/0.782, with Dipole and v-polarized illumination. Subsequently, PEB was carried out using a hot plate at 95° C. for 50 sec. Next, paddle development was carried out using a 2.38% by mass aqueous tetramethylammoniumhydroxide solution as a developer solution for 10 sec with a GP nozzle of a development unit, followed by rinsing with ultra pure water. Spin drying was conducted at 2,000 rpm for 15 sec to obtain a substrate on which a resist pattern was formed. In this process, an exposure dose at which a resist pattern with a line of 40 nm and a pitch of 80 nm was formed was designated as "optimal exposure dose", and this optimal exposure dose was regarded as sensitivity (mJ/cm$^2$). In the observation of the resist pattern with a line of 40 nm and a pitch of 80 nm resolved at the optimal exposure dose, line widths at arbitrary ten points were measured when observed from above the pattern using a SEM for critical dimension measurement: CG4000 manufactured by Hitachi, Ltd., and the degree of distribution of measurements expressed as a value in terms of the 3 Sigma was defined as "LWR (nm)". Uniformity of the line width of the pattern after development can be determined to be more favorable as the LWR value is smaller.

TABLE 1

| | (A) Component | | (B) Base polymer | | (C) Fluorine atom-containing polymer | | (D) Acid diffusion control agent | | (E) Solvent | | Sensitivity (mJ/cm$^2$) | LWR (nm) |
|---|---|---|---|---|---|---|---|---|---|---|---|---|
| | type | content (parts by mass) | type | content (parts by mass) | type | content (parts by mass) | type | content (parts by mass) | type | content (parts by mass) | | |
| Example 3 | A1-1 | 8 | B-1 | 100 | C-1 | 5 | D-1 | 0.6 | E-1/E-2/E-3 | 1,881/806/200 | 30 | 2.8 |
| Example 4 | A1-2 | 8.2 | B-1 | 100 | C-1 | 5 | D-1 | 0.6 | E-1/E-2/E-3 | 1,881/806/200 | 30 | 2.8 |
| Example 5 | A1-1 | 8 | B-1 | 100 | C-1 | 5 | D-2 | 0.7 | E-1/E-2/E-3 | 1,881/806/200 | 28 | 2.9 |
| Example 6 | A1-1 | 6 | B-1 | 100 | C-1 | 5 | D-3 | 1.8 | E-1/E-2/E-3 | 1,881/806/200 | 28 | 2.9 |
| Example 7 | A1-1 | 8 | B-1 | 100 | C-2 | 5 | D-1 | 0.6 | E-1/E-2/E-3 | 1,881/806/200 | 30 | 2.8 |
| Example 8 | A1-1 | 8 | B-1 | 100 | C-2 | 5 | D-1 | 0.7 | E-1/E-2/E-3 | 1,881/806/200 | 28 | 2.8 |
| Example 9 | A1-1 | 8 | B-1 | 100 | C-3 | 5 | D-1 | 0.7 | E-1/E-2/E-3 | 1,881/806/200 | 28 | 2.9 |
| Example 10 | A1-1 A1-2 | 4 4.1 | B-1 | 100 | C-2 | 5 | D-1 | 0.7 | E-1/E-2/E-3 | 1,881/806/200 | 28 | 2.7 |
| Example 11 | A1-1 A2-1 | 4 4.9 | B-1 | 100 | C-3 | 5 | D-1 | 0.7 | E-1/E-2/E-3 | 1,881/806/200 | 28 | 2.9 |
| Example 12 | A1-1 A2-2 | 4 4.3 | B-1 | 100 | C-3 | 5 | D-1 | 0.7 | E-1/E-2/E-3 | 1,881/806/200 | 28 | 2.9 |
| Comparative Example 1 | A2-1 | 9.7 | B-1 | 100 | C-1 | 5 | D-1 | 1.1 | E-1/E-2/E-3 | 1,881/806/200 | 28 | 3.8 |
| Comparative Example 2 | A2-2 | 8.5 | B-1 | 100 | C-1 | 5 | D-1 | 1.1 | E-1/E-2/E-3 | 1,881/806/200 | 28 | 3.8 |
| Comparative Example 3 | A2-1 | 8 | B-1 | 100 | C-1 | 5 | D-2 | 1.1 | E-1/E-2/E-3 | 1,881/806/200 | 28 | 3.6 |

As is clear from the results shown in Table 1, the resist pattern formed from the radiation-sensitive resin composition was revealed to have satisfactory LWR.

According to the embodiments of the present invention, a radiation-sensitive resin composition capable of forming a resist pattern having satisfactory LWR can be provided. Also, in the method for forming a resist pattern using the radiation-sensitive resin composition, a liquid immersion lithography step can be also employed and a finer resist pattern can be formed, and is suitable also for a lithography process by which microfabrication is expected to further advance in the future.

Obviously, numerous modifications and variations of the present invention are possible in light of the above teachings. It is therefore to be understood that within the scope of the appended claims, the invention may be practiced otherwise than as specifically described herein.

The invention claimed is:

1. A radiation-sensitive resin composition comprising:
   a polymer; and
   an acid generating agent to generate a compound represented by formula (1-1) by irradiation with a radioactive ray:

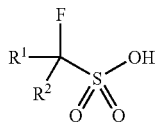

(1)

wherein, in the formula (1-1),
   $R^2$ represents a hydrogen atom;
   X represents a carbonyloxy group; and
   $R^3$ represents a monovalent alicyclic hydrocarbon group having 3 to 20 carbon atoms, not having or having a substituent, and being monocyclic or polycyclic.

2. The radiation-sensitive resin composition according to claim 1, wherein the acid generating agent is a sulfonium salt compound or an iodonium salt compound.

3. The radiation-sensitive resin composition according to claim 1, wherein the substituent of the monovalent alicyclic hydrocarbon group represented by $R^3$ is a hydroxyl group, a thiol group, an aryl group or an alkenyl group.

4. The radiation-sensitive resin composition according to claim 1, wherein the monovalent alicyclic hydrocarbon group represented by $R^3$ is a substituted or unsubstituted polycyclic alicyclic hydrocarbon group.

5. The radiation-sensitive resin composition according to claim 1, wherein the monovalent alicyclic hydrocarbon group represented by $R^3$ is a substituted or unsubstituted adamantyl group.

6. The radiation-sensitive resin composition according to claim 1, wherein the monovalent alicyclic hydrocarbon group represented by $R^3$ is an adamantyl group which is unsubstituted or substituted with a hydroxyl group, a thiol group, an aryl group or an alkenyl group.

7. A method for forming a resist pattern, comprising:
   providing the radiation-sensitive resin composition according to claim 1 on a substrate to form a resist film;
   exposing the resist film formed; and
   developing the resist film exposed.

8. The method according to claim 7, wherein the exposing step is carried out by liquid immersion lithography.

9. An acid generating agent that generates a compound represented formula (1-1):

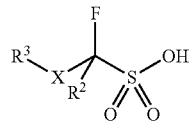

(1-1)

wherein, in the formula (1-1),
R² represents a hydrogen atom;
X represents a carbonyloxy group; and
R³ a monovalent alicyclic hydrocarbon group having 3 to 20 carbon atoms, not having or having a substituent, and being monocyclic or polycyclic.

10. The acid generating agent according to claim 9, wherein the substituent of the monovalent alicyclic hydrocarbon group represented by R³ is a hydroxyl group, a thiol group, an aryl group or an alkenyl group.

11. The acid generating agent according to claim 9, wherein the monovalent alicyclic hydrocarbon group represented by R³ is a substituted or unsubstituted polycyclic alicyclic hydrocarbon group.

12. The acid generating agent according to claim 9, wherein the monovalent alicyclic hydrocarbon group represented by R³ is a substituted or unsubstituted adamantyl group.

13. The acid generating agent according to claim 9, wherein the monovalent alicyclic hydrocarbon group represented by R³ is an adamantyl group which is unsubstituted or substituted with a hydroxyl group, a thiol group, an aryl group or an alkenyl group.

14. A compound represented by formula (1-1):

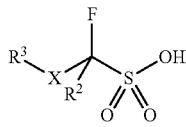

(1-1)

wherein, in the formula (1-1),

R² represents a hydrogen atom;

X represents a carbonyloxy group; and

R³ represents a monovalent alicyclic hydrocarbon group having 3 to 20 carbon atoms, not having or having a substituent, and being monocyclic or polycyclic.

15. The compound according to claim 14, wherein the substituent of the monovalent alicyclic hydrocarbon group represented by R³ is a hydroxyl group, a thiol group, an aryl group or an alkenyl group.

16. The compound according to claim 14, wherein the monovalent alicyclic hydrocarbon group represented by R³ is a substituted or unsubstituted polycyclic alicyclic hydrocarbon group.

17. The compound according to claim 14, wherein the monovalent alicyclic hydrocarbon group represented by R³ is a substituted or unsubstituted adamantyl group.

18. The compound according to claim 14, wherein the monovalent alicyclic hydrocarbon group represented by R³ is an adamantyl group which is unsubstituted or substituted with a hydroxyl group, a thiol group, an aryl group or an alkenyl group.

* * * * *